(12) United States Patent
Chen et al.

(10) Patent No.: US 7,700,353 B2
(45) Date of Patent: Apr. 20, 2010

(54) COMPOSITIONS AND METHODS FOR INDUCING APOPTOSIS IN TUMOR CELLS

(75) Inventors: Thomas T. Chen, Storrs, CT (US); Maria J. M. Chen, Storrs, CT (US)

(73) Assignee: E-P Therapeutics, Inc., Ridgefield, CT (US)

( * ) Notice: Subject to any disclaimer, the term of this patent is extended or adjusted under 35 U.S.C. 154(b) by 769 days.

(21) Appl. No.: 11/354,484

(22) Filed: Feb. 15, 2006

(65) Prior Publication Data

US 2006/0135429 A1 Jun. 22, 2006

Related U.S. Application Data

(63) Continuation-in-part of application No. 10/100,492, filed on Mar. 18, 2002, now Pat. No. 7,118,752, which is a continuation-in-part of application No. 09/669,642, filed on Sep. 26, 2000, now Pat. No. 6,610,302, which is a continuation-in-part of application No. 09/120,818, filed on Jul. 22, 1998, now Pat. No. 6,358,916.

(51) Int. Cl.
*C12N 5/00* (2006.01)
*C07K 14/65* (2006.01)
*A61K 38/30* (2006.01)

(52) U.S. Cl. .................. 435/375; 435/325; 435/366; 530/303; 530/399; 514/2; 514/3

(58) Field of Classification Search ............... None
See application file for complete search history.

(56) References Cited

U.S. PATENT DOCUMENTS

| | | | |
|---|---|---|---|
| 5,093,317 A | 3/1992 | Lewis | |
| 5,405,942 A | 4/1995 | Bell et al. | |
| 5,473,054 A | 12/1995 | Jameson et al. | |
| 5,476,779 A | 12/1995 | Chen et al. | |
| 6,221,842 B1 | 4/2001 | Goldspink | |
| 6,358,916 B1 | 3/2002 | Chen et al. | |
| 6,610,302 B1 | 8/2003 | Chen et al. | |
| 2004/0116335 A1 | 6/2004 | Chen et al. | |

FOREIGN PATENT DOCUMENTS

| | | |
|---|---|---|
| EP | 0 309 050 | 3/1989 |
| WO | WO 89/05822 | 6/1989 |
| WO | WO 93/23067 | 11/1993 |

OTHER PUBLICATIONS

Ehemann et al. Flow cytometric detection of spontaneous apoptosis in human breast cancer using the TUNEL-technique. Cancer Letter vol. 194, pp. 125-131 (2003).*
Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Chen, Maria J., Chiou, P. Peter, Yang, Bih-Yin, Lo, Hung Chieh, Son, Jin-Ki, Hendricks, Jeffrey, Bailey, George and Chen, Thomas T. Development of Rainbow Trout Hepatoma Cell lines and Determining the Effects of Rainbow Trout Pro-IGF-I Ea4-Peptide on Morphological Changes and Anchorage-Independent Cell Growth in These Cell Lines. In Vitro—Animals, 40: 118-128, 2004.
Chen, M.J., Kuo, Y.-H., Tian, X.C., and Chen, T.T. Novel Biological Activities of the Rainbow Trout Pro-IGF-I Ea-4-Peptide: Studies on Effects of Trout Pro-IGF-I Ea-4-Peptide on Morphological Change, Anchorage-Dependent Cell Division, and Invasiveness in Tumor Cells. Gen. Comp. Endpcrinol., 126: 342-351, 2002.
Duguay, S. J. Post-translational processing of insulin-like growth factors, Horm. Metab. Res., 31: 43-49, 1999.
Eferl, R., Ricci, R., Kenner, L., Zenz, R., David, Jean-Pierre, Rath, M. and Wagner, E.F. Liver tumor development: c-Jun antagonizes the proapoptotic activity of p53. Cell, 112: 181-192, 2003.
Kuo, Ya-Huei and Chen, T.T. Novel activities of pro-IGF-I E-peptides: regulation of morphological differentiation and anchorage-independent growth in human neuroblastoma cells. Experimental Cell Res., 280: 75-89, 2002.
Porter, A.G. and Janicke, R.U. Emerging roles of capase-3 in apoptosis. Cell Death and Differentiation, 6: 99-104, 1999.
Rotwein, P., Pollock, K. M., Didier, D. K., and Krivi, G. G. Organization and sequence of the human insulin-like growth factor I gene. Alternative RNA processing produces two insulin-like growth factor I precursor peptides. J. Biol. Chem,, 261: 4828-4832, 1986.
Tian, X. C., Chen, M. J., Pantschenko, A. G., Yang, T. J., and Chen, T. T. Recombinant E-peptides of pro-IGF-I have mitogenic activity. Endocrinology, 140: 3387-3390, 1999.

* cited by examiner

*Primary Examiner*—Marianne P Allen
*Assistant Examiner*—Regina M DeBerry
(74) *Attorney, Agent, or Firm*—McCarter & English, LLP

(57) ABSTRACT

A method is described for using an E-domain peptide for the induction of apoptosis in a cancer cells. In particular, the invention relates to methods for using a-type E-domain peptide from trout IGF and/or a b-type E-domain peptide from human IGF for the induction of apoptosis in a broad spectrum of cancer cells. The peptide species can be a homologue of the E-domain of IGF-1 or a fusion protein comprising the E-domain of IGF-1. It can be administered to one or more cancer cells alone or in a pharmaceutically acceptable composition.

9 Claims, 33 Drawing Sheets

```
hEb      (1)  RSVRAQRHTDMPKTQKYQPPSTNKNTKSQRRKGWPKTHPGGEQKEGTEASLQIRGKKEQRREIGSRNAECRGKKGK
Ea4      (1)  RSVRAQRHTDMPRTPKVSTAVQNVDRGTERRTAQHPDKTKTKKKPLSGHSHPSCKEVHQKNSSRGNTGGRNYRM---
Ea3      (1)  RSVRAQRHTDMPRTPKVSTAVQSVDRGTERRTAQHPDKTKPK-------KEVHQKNSSRGNTGGRNYRM---
Ea2      (1)  RSVRAQRHTDMPRTP----------------------------KKPLSGHSHPSCKEVHQKNSSRGNTGGRNYRM---
Ea1      (1)  RSVRAQRHTDMPRTP-----------------------------------KEVHQKNSSRGNTGGRNYRM---

Consensus (1) RSVRAQRHTDMPRTPK            T  RR  A        K  S  S        KEVHQKNSSRGNTGGRNYRM
```

Amino acid sequence alignment of hEb qnd rtEa-peptides.
Shaded areas show sequence identity

FIG. 1B

Magnification: 10 x 20

FIG. 8A(1) Control HT-29
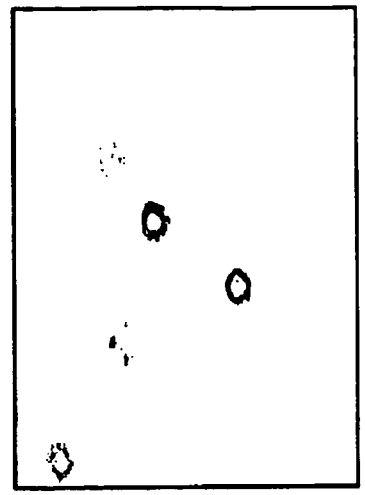
FIG. 8A(2) rtEa4 (1.6 mM)
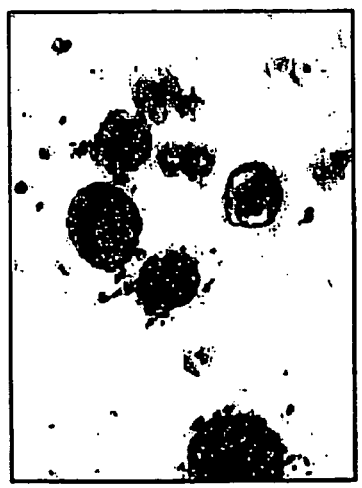
FIG. 8A(3) MDA-MB-231
FIG. 8A(4)

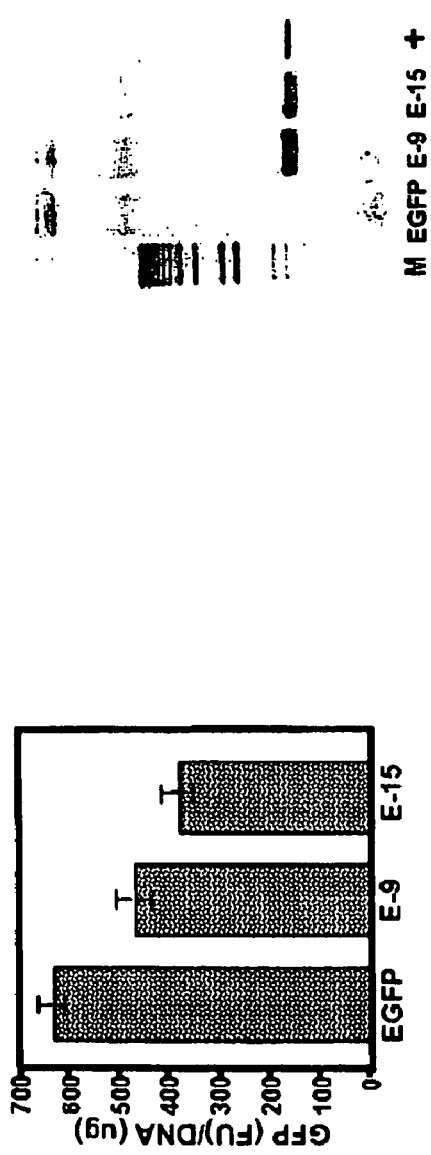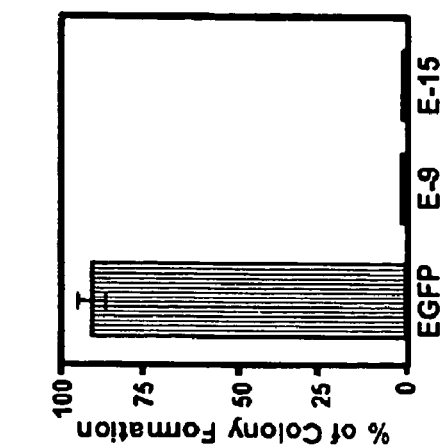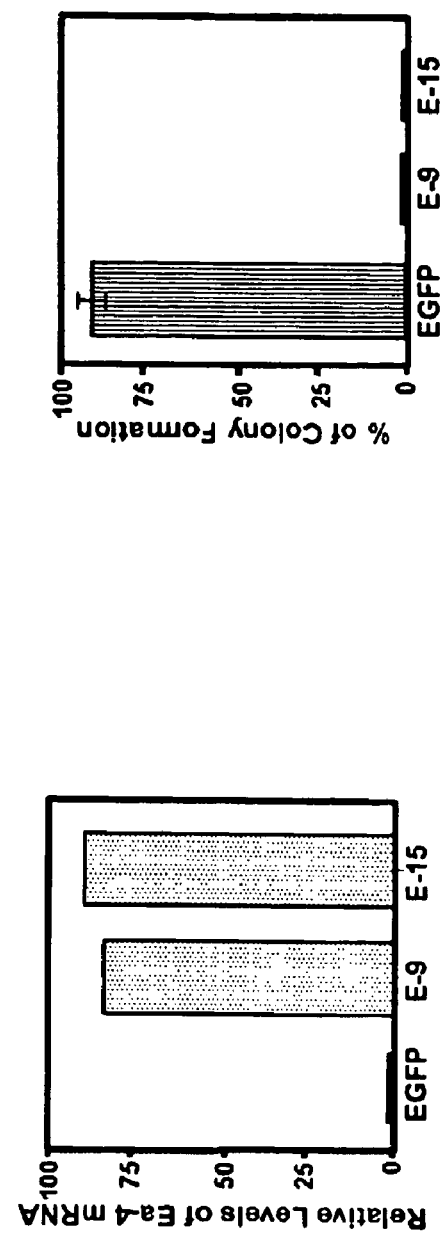
FIG. 10A  FIG. 10B  FIG. 10C  FIG. 10D

FIG. 10E(3)
FIG. 10E(2)
FIG. 10E(1)
FIG. 10H
FIG. 10G
FIG. 10F Morphological change of MDA-MB-231 cells transfected with hEb cDNA.

Colony formation activities of MDA-MB-231 cells transfected with hEb cDNA in a semi-solid medium.

Determination of the antiangiogenic activity of Ea4-peptide.

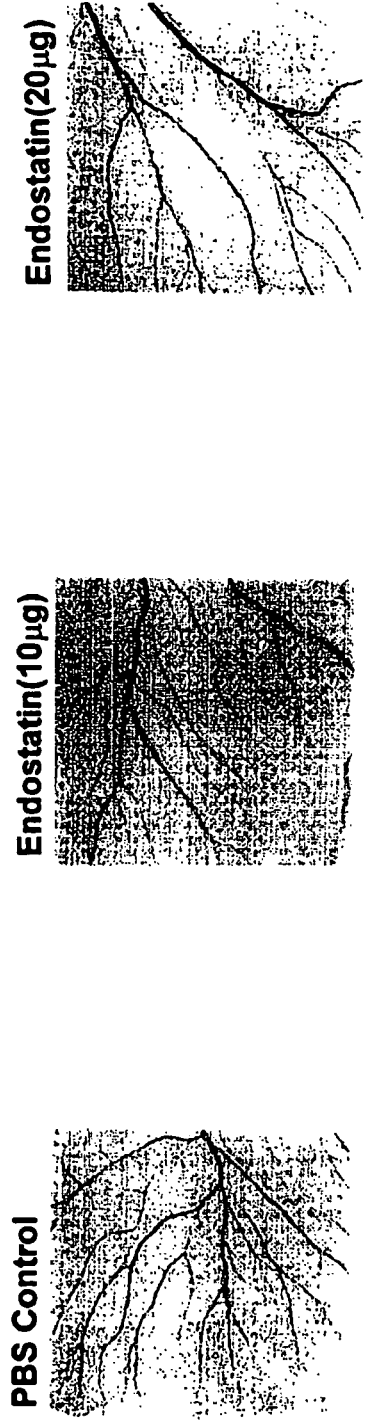
FIG. 18(1) PBS Control
FIG. 18(2) Endostatin(10μg)
FIG. 18(3) Endostatin(20μg)
FIG. 18(4) shEb(250μg)
FIG. 18(5) shEb(500μg)
FIG. 18(6) shEb(1000μg)

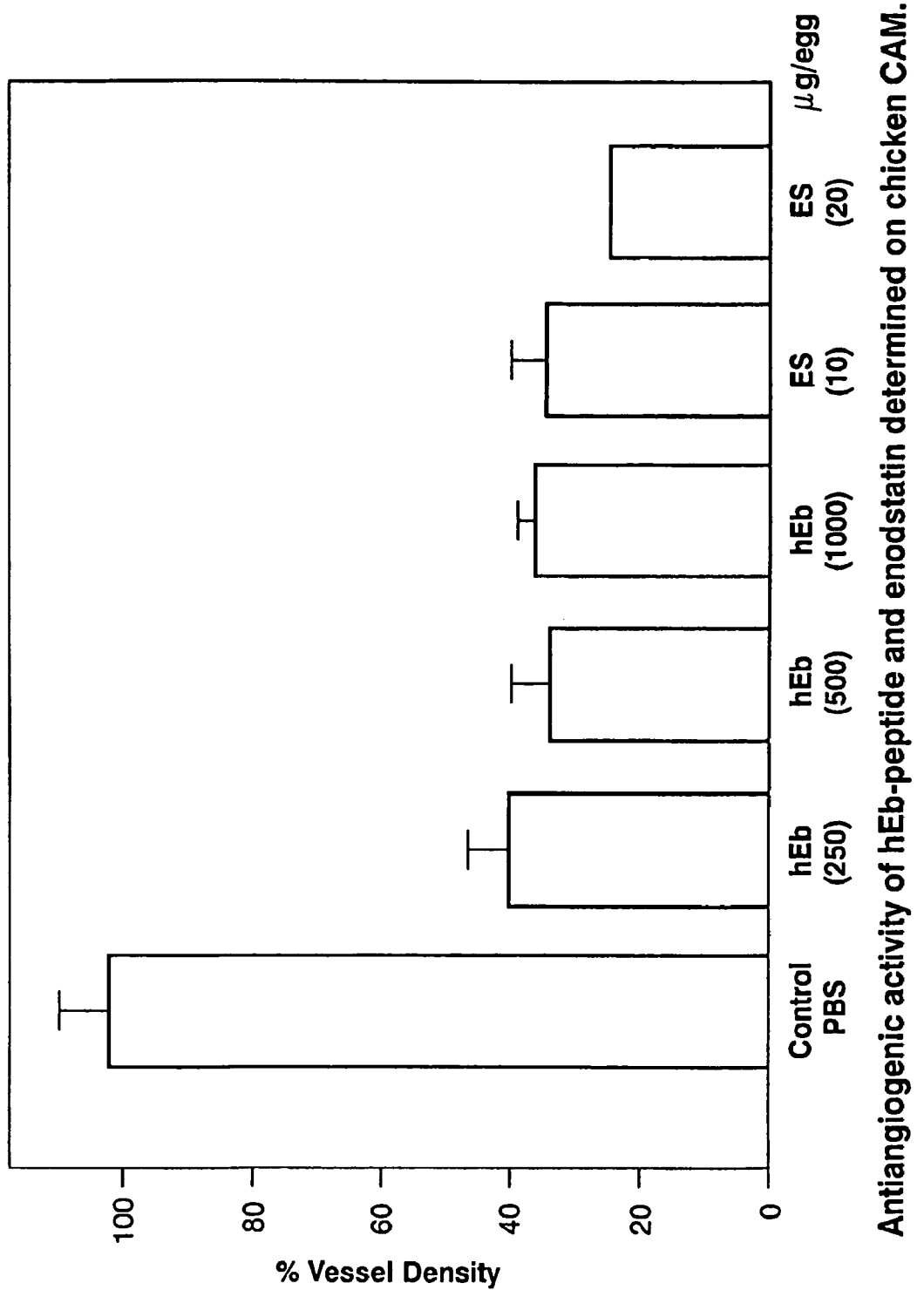

```
SEQUENCE LISTING

<160> NUMBER OF SEQ ID NOS: 7

<210> SEQ ID NO 1
<211> LENGTH: 77
<212> TYPE: PRT
<213> ORGANISM: Homo sapiens

<400> SEQUENCE: 1

Arg Ser Val Arg Ala Gln Arg His Thr Asp Met Pro Lys Thr Gln Lys
 1               5                  10                  15

Tyr Gln Pro Pro Ser Thr Asn Lys Asn Thr Lys Ser Gln Arg Arg Lys
            20                  25                  30

Gly Trp Pro Lys Thr His Pro Gly Gly Glu Gln Lys Glu Gly Thr Glu
        35                  40                  45

Ala Ser Leu Gln Ile Arg Gly Lys Lys Lys Glu Gln Arg Arg Glu Ile
    50                  55                  60

Gly Ser Arg Asn Ala Glu Cys Arg Gly Lys Lys Gly Lys
65                  70                  75

<210> SEQ ID NO 2
<211> LENGTH: 74
<212> TYPE: PRT
<213> ORGANISM: Oncorhynchus mykiss

<400> SEQUENCE: 2

Arg Ser Val Arg Ala Gln Arg His Thr Asp Met Pro Arg Thr Pro Lys
 1               5                  10                  15

Val Ser Thr Ala Val Gln Asn Val Asp Arg Gly Thr Glu Arg Arg Thr
            20                  25                  30

Ala Gln His Pro Asp Lys Thr Lys Thr Lys Lys Lys Pro Leu Ser Gly
        35                  40                  45

His Ser His Pro Ser Cys Lys Glu Val His Gln Lys Asn Ser Ser Arg
    50                  55                  60

Gly Asn Thr Gly Gly Arg Asn Tyr Arg Met
65                  70

<210> SEQ ID NO 3
<211> LENGTH: 62
<212> TYPE: PRT
<213> ORGANISM: Oncorhynchus mykiss

<400> SEQUENCE: 3

Arg Ser Val Arg Ala Gln Arg His Thr Asp Met Pro Arg Thr Pro Lys
 1               5                  10                  15

Val Ser Thr Ala Val Gln Ser Val Asp Arg Gly Thr Glu Arg Arg Thr
            20                  25                  30

Ala Gln His Pro Asp Lys Thr Lys Pro Lys Lys Glu Val His Gln Lys
```

```
              35                  40                  45
Asn Ser Ser Arg Gly Asn Thr Gly Gly Arg Asn Tyr Arg Met
     50                  55                  60

<210> SEQ ID NO 4
<211> LENGTH: 47
<212> TYPE: PRT
<213> ORGANISM: Oncorhynchus mykiss

<400> SEQUENCE: 4

Arg Ser Val Arg Ala Gln Arg His Thr Asp Met Pro Arg Thr Pro Lys
 1               5                  10                  15

Lys Pro Leu Ser Gly His Ser His Pro Ser Cys Lys Glu Val His Gln
             20                  25                  30

Lys Asn Ser Ser Arg Gly Asn Thr Gly Gly Arg Asn Tyr Arg Met
         35                  40                  45

<210> SEQ ID NO 5
<211> LENGTH: 35
<212> TYPE: PRT
<213> ORGANISM: Oncorhynchus mykiss

<400> SEQUENCE: 5

Arg Ser Val Arg Ala Gln Arg His Thr Asp Met Pro Arg Thr Pro Lys
 1               5                  10                  15

Glu Val His Gln Lys Asn Ser Ser Arg Gly Asn Thr Gly Gly Arg Asn
             20                  25                  30

Tyr Arg Met
         35

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttgtggccg tttacgtc                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcacagcacc cagacaag                                                   18
```

COMPOSITIONS AND METHODS FOR INDUCING APOPTOSIS IN TUMOR CELLS

REFERENCE TO RELATED APPLICATIONS

This application is a continuation-in-part application of U.S. patent application Ser. No. 10/100,492, filed Mar. 18, 2002 now U.S. Pat. No. 7,118,752 (Notice of Allowance mailed: Nov. 15, 2005), which is a continuation-in-part application of U.S. patent application Ser. No. 09/669,642, filed Sep. 26, 2000, now U.S. Pat. No. 6,610,302, which is a continuation-in-part of U.S. patent application Ser. No. 09/120,818, filed Jul. 22, 1998, now U.S. Pat. No. 6,358,916, the disclosures of which are hereby incorporated by reference.

SEQUENCE LISTING

The present application hereby incorporates by reference, in its entirety, the Sequence Listing, and CRF of the Sequence Listing previously filed with the United States Patent and Trademark Office in association with the parent application, U.S. patent application Ser. No. 10/100,492 (U.S. Patent Publication #: U.S. 20040116335 A1); filed: Mar. 18, 2002; entitled: Compositions and methods for inhibiting the proliferation and invasiveness of malignant cells comprising E-domain peptides of IGF-I. A Sequence Listing for the present application is submitted herewith, which is identical to the Sequence Listing and CRF submitted for U.S. patent application Ser. No. 10/100,492.

FIELD OF THE INVENTION

The present invention relates generally to therapeutic uses of IGF-I peptides. In particular, the present invention relates to use of IGF-I E-domain peptides for inducing apoptosis in cancer cells.

BACKGROUND OF THE INVENTION

Insulin-like growth factors (IGF's) are mitogenic peptides that regulate embryonic development, post-natal growth and cellular differentiation in vertebrates. The functions of mature IGF peptides have been extensively studied in various in vitro and in vivo systems. IGF's, including IGF-I and IGF-II, are among the members of a family of structurally and evolutionarily related peptides that also include insulin and relaxins. Like many hormones, IGF's are initially translated as pre-pro-peptides that undergo post-translational processing to result in the mature peptides.

The mature form of mammalian IGF-I is a basic protein of 7.5-kDa. The pre-pro-peptides of the mammalian IGF-I consist of an amino-terminal signal peptide, followed by the mature peptide with B, C, A and D domains, and a carboxyl-terminal E domain (See FIG. 1A for a schematic representation). The signal peptide at the amino-terminal end and the E-domain peptide at the carboxy-terminal end of the pre-pro-peptide are proteolytically cleaved from the peptide to result in the mature, biochemically active species.

To date, multiple forms of pro-IGF-I have been identified in species from fish to mammals (Shamblott, Chen, Mol Mar Biol Biotechnol. 2: 351-61, 1993; Rotwein, Proc. Natl. Acad. Sci USA, 83:77-81, 1986). In humans, three alternative spliced isoforms of pro-IGF-I (pro-IGF-I-a pro-IGF-I-b and pro-IGF-I-c) have been reported (Rotwein, Proc. Natl. Acad. Sci USA, 1986; Rotwein, et al., J. Biol. Chem., 261: 4828-32, 1986; Chew, et al., Endocrinology, 136: 1939-44, 1995). These three pro-IGF-I isoforms differ only in the carboxyl-terminal E-domain regions that are normally removed in vivo from the mature IGF-I. The E-domains of pro-IGF-I-a, pro-IGF-I-b and pro-IGF-I-c contain 35, 77 and 40 amino acid residues, respectively. The first 15 amino acid residues at the N-terminus of E-domains (referred to as the common region) share identical sequences. The amino acid sequences following the common region vary between the three isoforms of human pro-IGF-I (see FIG. 1B).

Similar diversity of pro-IGF-I E-domains is also found in rainbow trout (*Oncorhynchus mykis*), where four different isoforms have been identified, designated for consistent reference herein as pro-IGF-I Ea-1, Ea-2, Ea-3 and Ea-4 (Shamblott, Chen, Mol. Mar. Biol. Biotech., 1993). Nucleotide sequence comparison of the four size forms of rainbow trout IGF-I mRNAs is consistent with the above observations concerning the Ea peptides in that the size differences among these mRNA species are due to insertions or deletions in the E domain regions of the molecules (See FIGS. 1A and 1B). The predicted amino acid residues of the common region of the four Ea peptides share identical sequences among themselves, as well as with pro-IGF-I E-peptides of human, mouse, and rat species (See FIG. 1B). The presence of the C-terminal 20 amino acid residues, sharing 70% identity with their human counterparts, identifies them as a-type E-peptides. The Ea-1 peptide of the rainbow trout (rt) pro-IGF-I (SEQ ID NO: 5) is a polypeptide of 35 amino acid residues, comprising the first 15 and the last 20 amino acid residues. Ea-2 (SEQ ID NO: 4) and Ea-3 (SEQ ID NO: 3) peptides differ from Ea-1 by virtue of either a 12- or 27-amino acid residue insertion between the first and last segments of the Ea-1-peptide sequence, respectively (see FIG. 1B). The Ea-4 peptide (SEQ ID NO: 2) contains both insertions. The predicted numbers of amino acid residues in each E-peptide are, thus, 35 (SEQ ID NO: 5), 47 (SEQ ID NO: 4), 62 (SEQ ID NO: 3) and 74 (SEQ ID NO: 2), respectively. There has not been any report on the presence of b-type IGF-I mRNA in rainbow trout (Shamblott and Chen, 1993).

FIG. 1B shows the amino acid sequences of the human Eb peptide (hEb) (SEQ ID NO:1) and the trout Ea peptides. Despite not having complete homology at the primary level, preliminary studies (unpublished data of this laboratory) indicate that hEb and trout Ea-4 peptide have very similar tertiary structures, particularly in the amino-terminal region containing the common sequences, and can compete effectively for binding to cell receptors specific to E-domain peptides.

Despite the presence of multiple E-domain variants, assigning biological function to the IGF E-domains has been elusive. Proteolytic processing of the pro-IGF's, resulting in the cleavage of E-domains from IGF's, is believed to be similar to the cleavage of the C-peptide of proinsulin (Foyt, et al., Insulin-Like Growth Factors: Molecular and Cellular Aspects, pp 1-16. Boca Raton: CRC press, 1991). In the past, it was generally accepted that E-domains, like the C-peptide of pro-insulin, possess little or no biological activity other than their potential roles in the biosynthesis of mature IGF. The C-peptide of pro-insulin is believed to have an essential function in the biosynthesis of insulin in linking the A and B chains in a manner that allows correct folding and inter-chain disulfide bond formation. In spite of the earlier reports indicating certain physiological effects of the insulin C-peptide (Johansson, et al., Diabetologia, 35: 121-28, 1992; Johansson, et al., Diabetologia, 35: 1151-58, 1992; Johansson, et al., J. Clin. Endo. Metab., 77: 976-81, 1993), it has not been widely accepted until recently. The C-peptide has now been shown to have many beneficial effects on various abnormalities in diabetic animal models and patients (Ido, et al., Science, 277: 563-66, 1997; Forst, et al., J. Clin. Invest. 101: 2036-41, 1998; Sjoquist, et al., Kidney Int., 54: 758-64, 1998). Moreover, recent studies further demonstrated specific binding of C-peptide to cell surfaces in a manner that suggests the presence of G-protein-coupled membrane receptors (Rigler, et al., Proc. Natl. Acad. Sci USA, 96: 13318-23, 1999). It is now thought that C-peptide may thereby stimulate specific intracellular signal transduction leading to the biological activities of C-peptide (Wahren, et al., Am. J. Physiol. Endo. Metab. 278: E759-68, 2000; Kitamura, et al., Biochem J., 355: 123-29, 2001).

Tian et al. (1999) have recently reported that recombinant rainbow trout Ea-2-, Ea-3- and Ea-4-peptides possess mitogenic activity in several non-transformed cell lines, including NIH 3T3 cells and caprine mammary epithelium cells (CMEC) (Panschenko et al., 1997). Since trout Ea-2- and Ea-4-peptide contains a signal motif for peptidyl C-terminal amidation (Shamblott and Chen, 1993; Barr, 1991), and a bipartite consensus nuclear localization sequence is also present in Ea-4-peptide (Shamblott and Chen, 1993; Dingwall and Laskey, 1991), the present inventors have concluded that these peptides potentially possess other novel biological activities. Thus, the present inventors demonstrate that novel biological activities are associated with both the Ea peptides of the rainbow trout pro-IGF-I, and with the human Eb peptide.

The present invention is based on the observation that in oncogenic cell lines, for example, human breast cancer cells, colon cancer cells, neuroblastoma cells, and trout hepatoma cells, Ea-peptides and human Eb-peptides induce morphological differentiation and inhibit anchorage-independent cell growth.

SUMMARY OF THE INVENTION

In the present invention the inventors surprisingly and unexpectedly discovered that E-domain peptides induce apoptosis in tumor or malignant cells and little or no significant adverse effect on normal cells. Thus, in another preferred embodiment, the invention comprises methods for inducing apoptosis in a cancer cell, in vitro. In a related aspect, the invention also includes methods for treating cancer in an animal in need thereof, for example a human, comprising administering an effective amount of an E-domain peptide, wherein the E-domain peptide induces apoptosis in a cancer cell, in vivo.

In one embodiment, the present invention provides a method of inhibiting the proliferation of malignant cells, comprising the step of administering to one or more malignant cells an effective amount of a peptide species comprising an E-domain of insulin-like growth factor I (IGF-I). Preferably, the malignant cells are of a type selected from the group consisting of breast cancer cells, colon cancer cells, hepatoma cells, neuroblastoma cells, ovarian cancer cells, and prostate cancer cells. Also preferably, in the practice of the method of the present invention, the peptide species comprises an a-type E domain or a b-type E domain of IGF-I. More preferably, the peptide species comprises a fish a-type E-domain. More preferably still, the peptide species comprises an E-domain of rainbow trout IGF-I. Even more preferably, the peptide species may comprise an E domain of rainbow trout IGF-I selected from the group consisting of Ea-2 and Ea-4. Alternatively, the peptide species comprises a human b-type E domain.

As used herein, the term "E-peptide" or "E domain peptide" refers to a peptide that forms an E domain of IGF-1 of a trout. The E domain peptide can also be part of a fusion protein comprising the amino acid sequence of an E domain peptide or an E domain peptide homolog, fused to an additional component.

In another aspect, the practice of the method of the present invention contemplates a peptide species that comprises a homologue of the E-domain of IGF-I, or a fusion protein comprising the E-domain of IGF-I.

According to another aspect of the present invention, the peptide species is administered; in a pharmaceutical composition comprising the peptide species and one or more pharmaceutically acceptable adjuvants. In an alternative embodiment, the peptide species is administered to the one or more malignant cells by transforming the cells with exogenous nucleic acid that results in expression of an E domain of IGF-I in the cell.

In yet another embodiment, the present invention provides a method of inhibiting the proliferation of malignant cells, comprising the step of administering to the malignant cell nucleic acid encoding a protein comprising an E-domain of IGF-I. Preferably, the malignant cells are of a type selected from the group consisting of breast cancer cells, colon cancer cells, hepatoma cells, neuroblastoma cells, ovarian cancer cells, and prostate cancer cells. Furthermore, the protein encoded by the nucleic acid administered according to the present invention comprises an a-type E domain or a b-type E domain of IGF-I. Alternatively, the protein comprises a homologue of the E domain of IGF-I, or a fusion protein comprising the E domain of IGF-I. Preferably, the encoded protein comprises an E-domain of rainbow trout IGF-I. More preferably, the encoded protein comprises an E domain of rainbow trout IGF-I selected from the group consisting of Ea-2 and Ea-4. Alternatively, the encoded protein comprises an E-domain of human IGF-I. Preferably, the encoded protein comprises an Eb domain of human IGF-I.

In an alternative embodiment, the present invention contemplates a method for reducing the invasiveness of malignant cells, comprising administering to one or more malignant cells an effective amount of a peptide species comprising an E-domain of insulin-like growth factor I (IGF-I). Preferably, the malignant cells are of a type selected from the group consisting of breast cancer cells, colon cancer cells, hepatoma cells, neuroblastoma cells, ovarian cancer cells, and prostate cancer cells. Also preferred is the method of the invention wherein the peptide species comprises an a-type E-domain or a b-type E-domain of IGF-I. More preferably, the peptide species comprises an E-domain of rainbow trout IGF-I. More preferably still, the peptide species comprises an E domain of rainbow trout IGF-I selected from the group consisting of Ea-2 and Ea-4. Alternatively, the present invention comprises a method wherein the peptide species comprises an E-domain of human IGF-I. Preferably, the peptide species comprises an Eb domain of human IGF-I.

Alternatively, the present invention contemplates a method wherein the peptide species comprises a homologue of the E domain of IGF-I, or a fusion protein comprising the E domain of IGF-I. In addition, the present invention provides a method wherein the peptide species is administered in a pharmaceutical composition comprising the peptide species and one or more pharmaceutically acceptable adjuvants. In an alternative embodiment, the peptide species is administered to the malignant cells by transforming the cells with exogenous nucleic acid that results in expression of an E-domain peptide of IGF-I in the cell.

In yet another embodiment, the present invention contemplates a method for reducing the invasiveness of malignant cells, comprising administering to one or more malignant cells nucleic acid encoding a protein comprising an E-domain of IGF-I. Preferably, the malignant cells are of a type selected from the group consisting of breast cancer cells, colon cancer cells, hepatoma cells, neuroblastoma cells, ovarian cancer cells, and prostate cancer cells. In addition, the method contemplates nucleic acid encoding a protein that comprises an a-type E-domain or a b-type E-domain of IGF-I. Preferably, the encoded protein comprises an E-domain of rainbow trout IGF-I. More preferably, the encoded protein comprises an E-domain of rainbow trout IGF-I selected from the group consisting of Ea-2 and Ea-4. Alternatively, the protein comprises an E-domain of human IGF-I. Preferably, the protein comprises an Eb domain of human IGF-I. In another aspect, the protein comprises a homologue of the E-domain of IGF-I, or a fusion protein comprising the E-domain of IGF-I. In yet another aspect of the method of the invention, the nucleic acid is administered to the one or more malignant cells by transforming the cells with the nucleic acid.

In an alternative embodiment, the present invention includes a method of inhibiting angiogenic activity within animal tissue, the method comprising the step of exposing the tissue to an effective amount of a peptide species comprising an E-domain of insulin-like growth factor I (IGF-I). Alternatively, the peptide species comprises a homologue of the E domain of IGF-I, or a fusion protein comprising the E domain of IGF-I. Preferably, the peptide species comprises an E-domain of rainbow trout IGF-I. More preferably, the encoded protein comprises an E-domain of rainbow trout IGF-1 selected from the group consisting of Ea-2 and Ea-4. Alternatively, the peptide species comprises an E-domain of human IGF-I. More preferably, the peptide species comprises a b-type E domain of human IGF-I.

In yet another embodiment, the present invention provides a method for inhibiting the growth of human tissue comprising a vascularized mass of malignant cells, the method comprising the step of exposing the tissue to an effective amount of a peptide species comprising an E-domain of insulin-like growth factor I (IGF-I). Preferably, the malignant cells are of a type selected from the group consisting of breast cancer cells, colon cancer cells, hepatoma cells, neuroblastoma cells, ovarian cancer cells, and prostate cancer cells. According to this embodiment of the present invention, the peptide species comprises a homologue of the E domain of IGF-I, or a fusion protein comprising the E domain of IGF-I. Alternatively, the peptide species comprises an E-domain of human IGF-I. Preferably, the peptide species comprises a b-type E domain of human IGF-I.

BRIEF DESCRIPTION OF THE DRAWINGS

FIG. 1B shows the amino sequence alignment of hEb (SEQ ID NO: 1), rtEa-4 (SEQ ID NO:2), rtEa-3 (SEQ ID NO:3), rtEa-2 (SEQ ID NO: 4), and rtEa-1 (SEQ ID NO: 5).

FIG. 10 illustrates the effect of Ea-4-peptide cDNA transfected into MDA-MB 231 cells. EGFP, transfectants carrying EGFP gene alone; E-9 and E15, different transfectants carrying Ea-4-peptide and EGFP genes. (A) Levels of EGFP in MDA-MB-231 transfectants; (B) Detection of Ea-4-peptide gene in transfectants by PCR; (C) Relative levels of Ea-4-peptide mRNA determined by comparative RT-PCR; (D) Colony formation activity of MDA-MB-231 transfectants in a semi-solid agar medium; (E) Phase contrast micrographs of MDA-MB-231 transfectants with and without Ea-4-peptide cDNA; (F) Morphology of untransfected MDA-MB-231 cells cultured in growth medium supplemented with 50% of culture medium harvested from EGFP cells; (G) and (H) Morphology of untransfected MDA-MB-231 cells cultured in growth medium supplemented with 25% or 50% of culture medium harvested from E-15 cells. EGFP, transfectant carrying EGFP alone; E-9 and E-15, transfectants carrying Ea-4-peptide cDNA. The magnification of the micrographs is 200.times.

FIG. 18 depicts antiangiogenic activity on chicken chorioallantoic membrane ("CAM"). Depicted are the effects of control (PBS), endostatin (a known antiangiogenic agent), and the hEb peptide.

FIG. 19 is a graphical representation of the antiangiogenic activity of hEb-peptide and endostatin as determined on chicken CAM.

DETAILED DESCRIPTION OF THE INVENTION

Figure 1A:
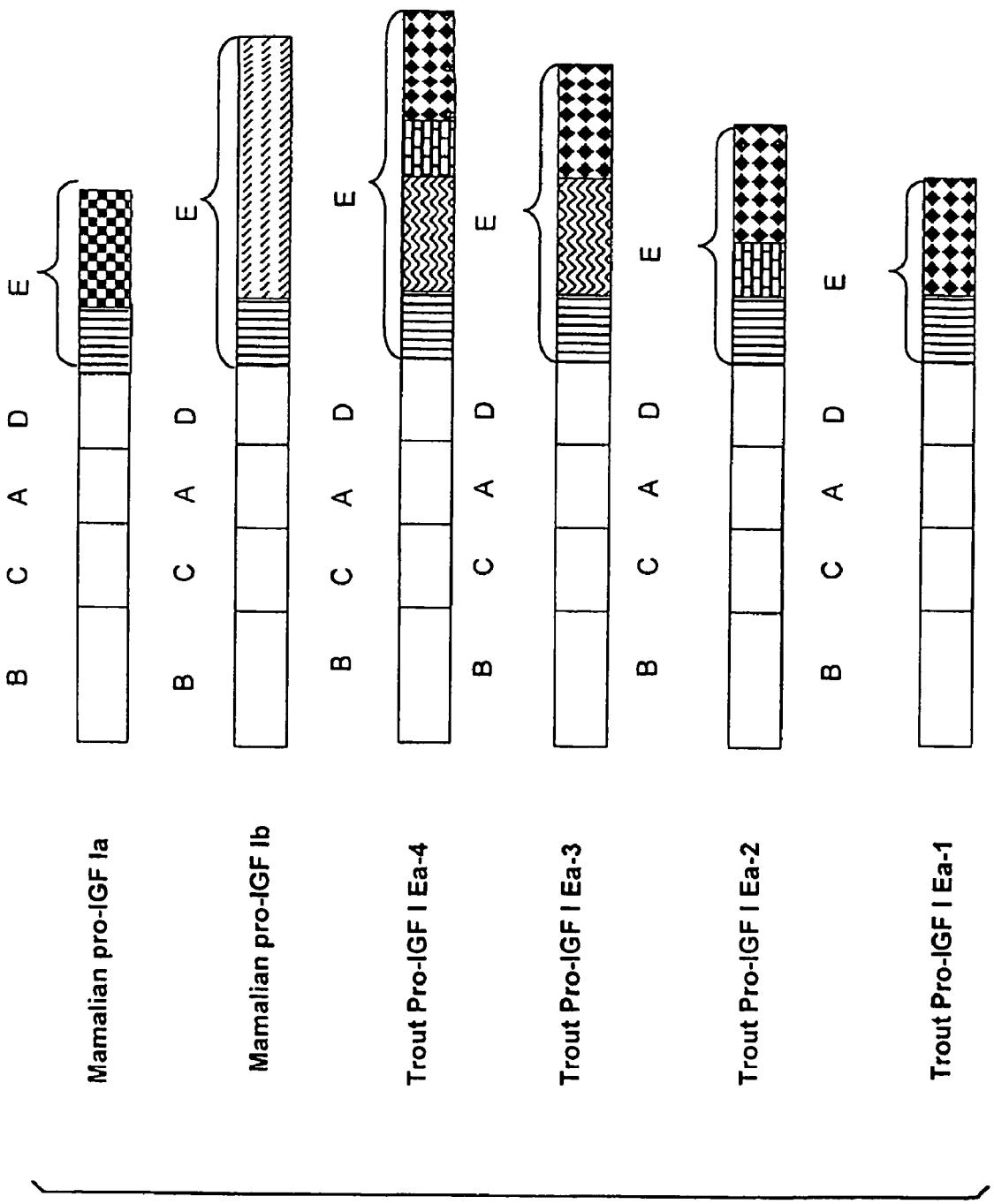
FIG. 1A is a schematic representation of the subforms of mammalian and rainbow trout pro-IGF-1 pro-peptides. B, C, A, D, and E indicate different domains of the IGF-1 peptides.

The present invention provides a method and compositions comprising IGF-I E-domain peptides with utility for inhibition of the proliferation and invasiveness of a broad spectrum of malignant cells, as well as for antiangiogenic activity. In particular, the present invention describes methods and compositions for inducing apoptosis in a tumor or malignant cell, in vitro and in vivo.

Recent attention has been focused on the biological activities of the proteolytically-processed polypeptides from post-translational modified peptide hormones. As discussed above, the C-peptide of pro-insulin has long been regarded to be biologically inactive except for a possible role in the folding of the insulin molecule during its post-translational modification. However, Ito et al. (1997) have reported that the C-peptide of pro-insulin was important in restoring vascular and neural dysfunction and Na+/K+-dependent ATPase activity in diabetic rats. Although a synthetic peptide amide of human b-type IGF-I E-peptide has been shown to exert mitogenic activity (Siefried et al., 1992), the biological activity of the native human E-peptides has not previously been identified.

Multiple alternative spliced forms of IGF-I transcript have been identified in mouse and rat (Roberts, et al., Mol. Endocrinol. 1: 243-48, 1987; Shimatsu, et al., J. Biol. Chem. 262: 7894-900, 1987). The alternative splicing of exon 5, resulting in variations in the E-domain of pro-IGF-I (Ea or Eb), has been shown to display developmental regulation and tissue specificity (Lin, et al, J. Endocrinol. 160: 461-67, 1999; Lin et al., Growth Horm IGF Res. 8: 225-33, 1998). Like mature IGF-I, as discussed in general above, the amino acid sequences of mouse or rat E-domains are highly homologous to their human counterparts. The biological significance of this conserved diversity of the E-domain and its differential expression is not clear. However, it is suggestive of potential biological activities associated with E-domain peptides. The presence of glycosylation sites on pro-IGF-I E-domains and the detection of such glycosylated products further suggest potential biological activity of E-domain peptides (Duguay, et al., J. Biol. Chem. 270: 17566-74, 1995). Indeed, a synthetic peptide amide with a 23-amino-acid sequence from the human pro-IGF-Ib E-domain (103-124) has been shown to possess mitogenic activity in human bronchial epithelial cells (Siegfried, et al., Proc. Natl. Acad. Sci. USA 89: 8107-11, 1992).

Recombinant Ea-2, Ea-3 and Ea-4 peptides of rainbow trout pro-IGF-I possess mitogenic activity in cultured BALB/3T3 fibroblast (Tian, et al., Endocrinology, 140: 3387-90, 1999). In addition to mitogenic activity, trout pro-IGF-I Ea-2 and Ea-4 peptides possess activities including induction of morphological change, enhancement of cell attachment, restoration of anchorage-dependent cell division behavior, and reduction of the invasiveness of aggressive cancer cells. Since similar morphological change has also been induced in a hepatoma cell line of Peoceliposis lucida (desert guppy) by treatment with the trout Ea-4 peptide, this observation rules out the possibility that the effects of trout pro-IGF-I Ea-4-peptide on human cancer cells are the consequence of artifact. The present invention confirms that the proteolytically cleaved Ea-4-peptide of rainbow trout pro-IGF-I has novel biological activities. These activities include induction of morphological change, eliminating anchorage independent cell division, reducing invasive activity of cancer cells, and inhibiting angiogenesis. In addition, the present invention confirms that a similar spectrum of activity is exhibited by the human Eb peptide of IGF-I.

Thus, the present inventors have demonstrated that novel biological activities are associated with both the Ea peptides of the rainbow trout pro-IGF-I and with the human Eb peptide.

To address the biological functions of human pro-IGF-I E-peptides, synthetic E-peptides (hEa and hEb) were generated. The characteristics of neuroblastoma cells to proliferate as well as to differentiate have made them an excellent in vitro system for studying the regulation of growth and differentiation. Thus, the present inventors have extensively characterized the biological activities of rainbow trout Ea-4 peptides in a neuroblastoma cell line (SK-N-F1) as a model system. To test if the biological activities of E-peptides are conserved in fish and humans, they tested the activities of synthetic human pro-IGF-I E-peptides in SK-N-F1 neuroblastoma cells. In the Examples presented herein, it is demonstrated that the human Eb-peptide of pro-IGF-I, like the rainbow trout Ea-4 peptide, possesses unique biological activities in inducing morphological differentiation and inhibiting anchorage-independent growth.

The present invention discloses the surprising and unexpected result that E-domain peptides can induce apoptosis in tumor or malignant cells in a dose dependent manner. Thus, in another preferred embodiment, the invention comprises methods for inducing apoptosis in a cancer cell, in vitro. In a related aspect, the invention also includes methods for treating cancer in an animal in need thereof, for example a human, comprising administering an effective amount of an E-domain peptide, wherein the E-domain peptide induces apoptosis in a cancer cell, in vivo.

In the methods of the invention, the particular E-domain peptide treatment used to induce apoptosis comprises, for example rtEa4- and/or hEb-peptide, and optionally includes an adjuvant, a carrier (e.g., a protein, lipid, glycol, glyceride, antioxidant, saccharide, or the like), or another biologically active agent, for example, an analgesic or anti-inflammatory (e.g., aspirin, an NSAID, a COX inhibitor, or the like), an anesthetic, an anti-angiogenic (e.g., angiostatins or endostatin), a chemotherapeutic, a cytotoxic agent (e.g., antimetabolites, antibiotics, alkylating agense, alkaloids), an antineoplastic agent (e.g., cytokines, antibodies, vaccines), a hormonal agent (e.g., LHRH agonists, anti-androgens, anti-estrogens, aromatase inhibitors, progestagens) or the like.

In addition, the E-domain treatment in any of the embodiments described herein may be delivered via any pharmacological acceptable route, for example, oral, topical, anal, intravenous, enteral, parenteral, subcutaneous, intramuscular, transdermal, intracapsular, intraspinal, intracranial, or the like. Furthermore, in any of the embodiments described herein the E-domain peptide may be delivered in any pharmaceutically acceptable forms, for example, a powder, a liquid (e.g., a spray, intravenous solution), a gel, a polymeric matrix, a pill or capsule (e.g., a controlled release capsule, a time release capsule, or both), subdermal implant, and the like. The above referenced compositions are given by way of example and are not to be construed as limiting on the scope of the present claims. Indeed, the E-domain therapeutic of the present invention can be delivered in any number of pharmaceutically acceptable forms and routes, which will be readily apparent to those of ordinary skill in the art.

The present invention is further illustrated and described by the following examples, which are not intended to limit the scope of the invention in any way.

Example 1

Cell Lines and Cell Culture Conditions

The following conditions were used for routine maintenance of cell cultures. Human breast cancer cells (MCF-7, ZR-75-1 and MDA-MB-231 cells) were obtained from American Type Cell Collection (ATCC, Rockville, Md.). They were cultured in F12/DMEM supplemented with 10% fetal bovine serum (FBS) and 10 ng/ml of insulin. Human colon cancer cells (HT-29 cells from ATCC) were cultured in F12/DMEM supplemented with 10% FBS; human HT1080 cells cultured in RPMI 1640 medium with 10% FBS; human hepatoma cells (HepG2 cells from ATCC), transformed human embryonic kidney cells (293GP cells, kindly provided by Dr. J. C. Burns at the University of California—San Diego) and human neuroblastoma cells (SK-N-F1 cells from ATCC) cultured in DME medium with high concentration of glucose and 10% FBS; and *Poeceliposis lucida* hepatoma cells (HC, kindly provided by Dr. Larry Hightower at the University of Connecticut) cultured in $CO_2$-independent medium supplemented with 10% FBS. All cell cultures were incubated at 37.degree. C. under a humidified atmosphere of 5% $CO_2$, except HC cells that were incubated at 30.degree. C. All tissue culture media and supplements used in this study were purchased from Gibco-BRL (Rockville, Md.).

Cells under various treatment conditions were maintained at 37.degree. C. in a 5% $CO_2$ incubator and observed from 30 minutes to 72 hours after incubation (synthetic human Ea- and Eb-peptide were chemically synthesized at the Biotechnology Center, University of Connecticut). For treatment with synthetic hEa, hEb peptide or hIGF-I, $1.times.10.sup.5$ cells were plated in each well of a 12-well culture plate in DMEM/F12 (1:1) supplemented with 0.4-3.2 .mu.M of synthetic hEa-, hEb-peptide and/or 5-10 nM of hIGF-I.

Example 2

Transfection of Cancer Cells with a Construct Comprising Trout Ea-4 cDNA

Figure 9A:
FIG. 9 A-C, is a schematic representation of the gene constructs used in the transfection of target cells. IGF-I-sp: signal peptide of hIGF-I; Ea-4 cDNA: cDNA of rtEa-4-peptide; hEb cDNA: cDNA of the human Eb peptide; EGFP: coding region of the enhanced green fluorescent protein gene; IRES: internal ribosome entry site.
Figure 9B:
Figure 9C:
Figure 11D:
FIG. 11 is an illustration of the morphological effects of hEa-, hEb-peptide and hIGF-1 in SK-N-F1 neuroblastoma cells. Morphology of SK-N-F1 neuroblastoma cells is shown in the eight upper sections labeled (A)-(H). Cells incubated without any addition of growth factors of peptides (A) or with 5 nM hIGF-1 alone (E) remain rounded and form aggregated clusters, similar to the morphology of the cells treated with synthetic 3.2 µM hEa-peptide alone (B) or in combination with 5 nM hIGF-1 (F). In contrast, SK-N-F1 cells treated with synthetic hEb-peptide (C) 1.6 µM synthetic hEb; (D) 3.2 µM hEb1; (G) 1.6 µM hEb+5 µM hIGF-1; (H) 3.2 µM hEb+5 µM hIGF-1.
FIG. 11I shows the dose response and time course of hEb-peptide induced neurite-like process outgrowth.
Figure 11H:
Figure 11C:
Figure 11G:
Figure 11B:
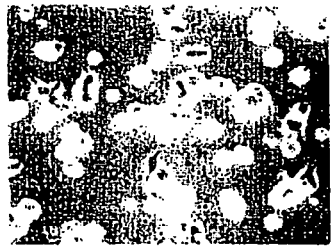
Figure 11F:
Figure 11A:
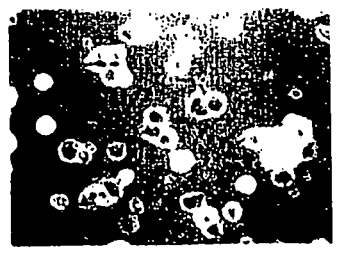
Figure 11E:
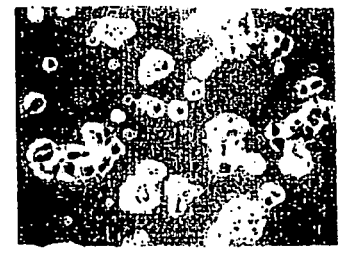
Figure 11I:
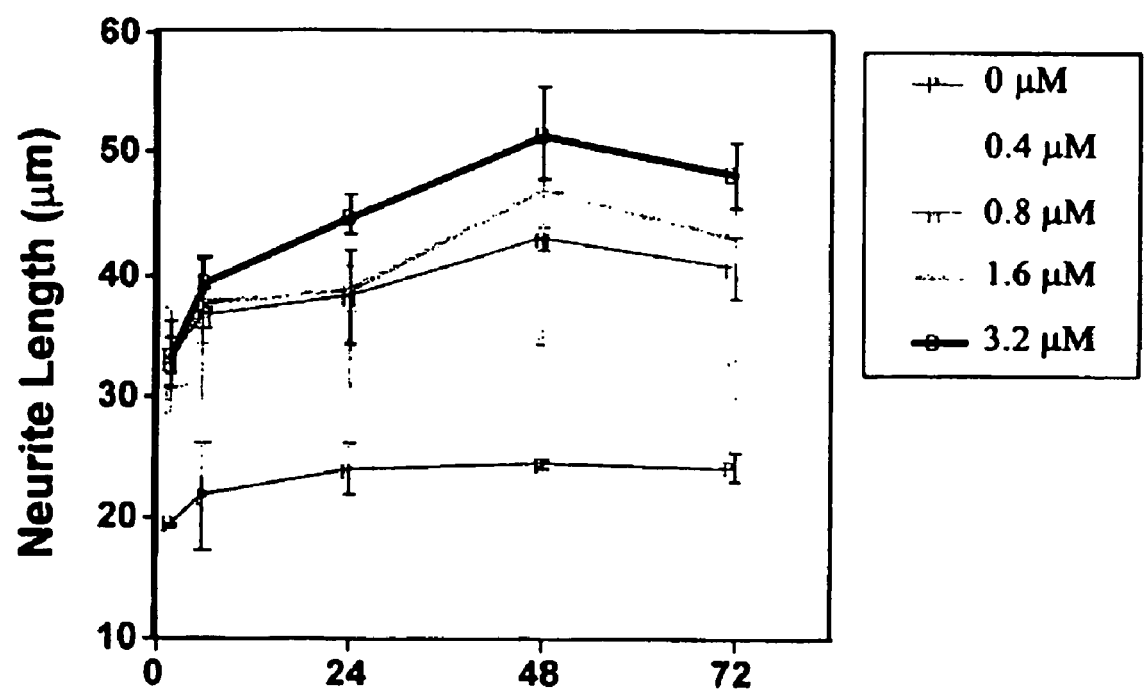

Two gene constructs, CMV-IGF-1-sp-Ea-4-cDNA-IRES-EGFP and CMV-IRES-EGFP were used in the transfection studies. The first construct (FIG. 9A) contained Ea-4 peptide cDNA (with a signal peptide sequence derived from hIGF-I), a ribosome re-entry site (IRES) and an enhanced green fluorescence protein (EGFP) marker gene. The other gene construct (FIG. 9C) contained IRES and EGFP, but did not contain Ea-4-peptide cDNA. The expression of both gene constructs was driven by a promoter from CMV. Vectors containing the recognized control sequences and marker gene are available from commercial sources (CLONTECH, Palo Alto, Calif.).

Transfection of the cells was accomplished as follows. MDA-MB-231 cells were cultured in F12/DMEM supplemented with 10% FBS and 10 ng/ml of insulin to 90% confluence. About $5.times.10.sup.6$ cells were harvested and resuspended in 1 mL of serum-free F12/DMEM containing 20 .mu.g of un-linearized constructs. The cells were electroporated in a BRL Cell-Porator using the following settings: low .OMEGA., 1180 micro Faraday (.mu.F) capacitance, and two pulses at 200 volts. Following electroporation, cells were resuspended in 12 mL of fresh growth medium and seeded into a 6-well plate to recover. Permanent transfectants expressing green fluorescence protein (GFP) were enriched in a medium containing neomycin (G418) at 1 mg/mL for ten days and followed with 500 .mu.g/mL for continuous maintenance. Individual green cell clones of transfectants were isolated from the enriched population by the method of serial dilution.

The presence of the transgene and the expression of Ea-4 (SEQ ID NO: 2) in transfectants were determined by PCR and comparative RT-PCR assays following conditions described by Greene et al. (1999). Ea-4-peptide specific primers used in the amplification were: forward primer (5'-CTTGTGGC-CGTTTACGTC-3') (SEQ ID NO 6); AND reverse primer (5'-GCACAGCACCCAGACAAG-3') (SEQ ID NO 7).

Results of PCR analysis of genomic DNA isolated from transfectants confirmed that clones E-9 and E-15 contained Ea-4-peptide cDNA, whereas control EGFP clones did not (FIG. 10B). Comparative RT-PCR analysis showed that about same levels of mRNA for Ea-4-peptide were detected in both clones E-9 and E-15, while no Ea-4 mRNA was detected in EGFP control clones (FIG. 10C). Soft Agar Colony Formation assay showed that while EGFP-transfected MDA-MB-231 cell clones formed colonies on soft agar medium, none of the Ea-4-peptide gene transfected MDA-MB-231 clones (ie., E9 and E15) form any colonies in soft agar medium (FIG. 10D), suggesting that the colony formation activity of MDA- MB-231 cells is abolished by the Ea-4 peptide. Furthermore, obvious morphological changes were also observed in MDA-MB-231 transfected cells expressing the Ea-4-peptide gene (FIG. 10E).

Because the signal peptide sequence of human IGF-I was also included in the Ea-4 cDNA transgene, the Ea-4 peptide produced by the transfected cell clones would be secreted into the medium. To confirm this, media isolated from EGFP clone and E15 clone were tested for their activities to induce morphological change in untransfected MDA-MB-231 cells. Results presented in FIGS. 10F, 10G and 10H showed that while medium isolated from E15 clone was able to induce the morphological change of untransfected MDA-MB-231 cells, medium isolated from EGFP cells could not. Therefore, these results rule out the possibility that any contaminant from the *E. coli* extract could result in the anti-tumor activity observed above.

Example 3

Transfection of Cancer Cells with a Construct Comprising hEb cDNA

Two gene constructs, CMV-IG F-1-sp-hEb-cDNA-IRES-EGFP and CMV-IRES-EGFP were used in the transfection studies. The first construct (FIG. 9B) contained hEb peptide cDNA (with a signal peptide sequence of hIGF-1), a ribosome re-entry site (IRES) and an enhanced green fluorescence protein (EGFP) marker gene. The other gene construct (FIG. 9C) contained IRES and EGFP, but did not contain hEb-peptide cDNA. The expression of both gene constructs was driven by a promoter from CMV.

Transfection of the cells was accomplished as follows. MDA-MB-231 cells were cultured in F12/DMEM supplemented with 10% FBS and 10 ng/ml of insulin to 90% confluence. About $5 \times 10^6$ cells were harvested and resuspended in 1 mL of serum-free F12/DMEM containing 20 $\mu$g of un-linearized constructs. The cells were electroporated in a BRL Cell-Porator using the following settings: low $\Omega$, 1180 micro Faraday ($\mu$F) capacitance, and two pulses at 200 volts. Following electroporation, cells were resuspended in 12 mL of fresh growth medium and seeded into a 6-well plate to recover. Permanent transfectants expressing green fluorescence protein (GFP) were enriched in a medium containing neomycin (G418) at 1 mg/mL for ten days and followed with 500 $\mu$g/mL for continuous maintenance. Individual green cell clones of transfectants were isolated from the enriched population by the method of serial dilution.

The presence of the transgene and the expression of hEb in transfectants were determined by PCR and comparative RT-PCR assays following conditions described by Greene et al. (1999). hEb-peptide specific primers used in the amplification were: forward primer (5'-CTTGTGGCCGTTTACGTC-3') (SEQ ID NO 6); AND reverse primer (5'-GCACAGCAC-CCAGACAAG-3') (SEQ ID NO: 7).

Example 4

Morphological Changes Induced by Rainbow Trout Ea-4 Peptides and Synthetic Human Analogues Approximately $1-2 \times 10^5$ of MCF-7, ZR-75-1, HT-29, HepG2, 293GP, HC or SK-N-F1 cells re-suspended in their respective basal medium without fetal bovine serum (FBS) were plated in a 6-well culture chamber. Prior to plating cells, an acid-washed coverslip was placed in each well of the culture chamber. Recombinant rainbow trout E-peptides (rtEa-2, rtEa-3 or rtEa-4 peptide at 0.8 $\mu$M), human IGF-I (hIGF-1, 2.5 nM) or the same amount of control protein was added to each well and the cell cultures were incubated at 37.degree. C. under a humidified atmosphere of 5% $CO_2$. The control protein was prepared from *E. coli* cells carrying the expression plasmid but without the E-peptide gene according to the purification method described by Tian et al. (1999). Coverslips were removed from the culture chamber 24 hours after initiation of the treatment and observed under an Olympic inverted microscope equipped with differential interference phase contrast objective lenses or phase contrast objective lens (final magnification, 200.times.). The morphological change assay was performed at least 10 times with different batches of Ea-4 peptide preparations.

Effects of Ea-1sp, Ea-2sp, Ea-3sp and Ea-4sp on induction of morphological change were assayed in ZR-75-1 cells following the same method described above. The concentration of these synthetic peptides tested was 0.4 $\mu$M.

Morphological Changes Induced by Rainbow Trout Ea Peptides

Figure 2A:
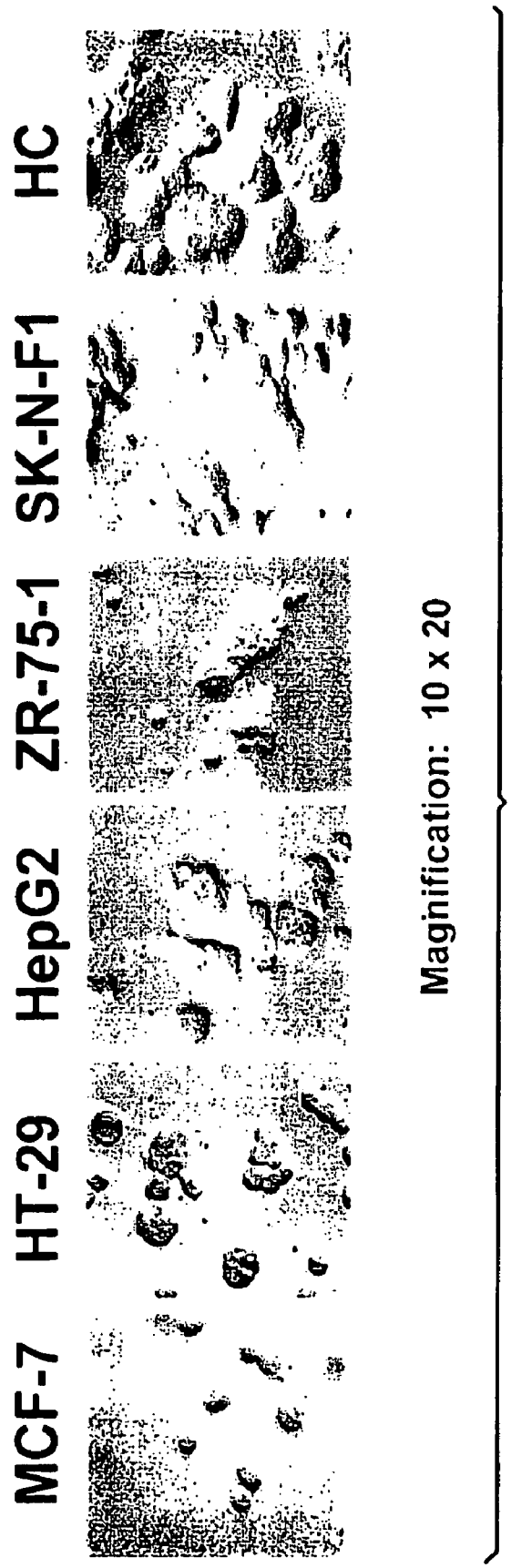
FIG. 2 A-C, depicts morphological changes in different tumor cells (MCF-7, HT-29, HepG2, ZR-75-1, SK-N-F1, HC, respectively) induced by the Ea-4-peptide of trout pro-IGF-I.
Figure 2B:
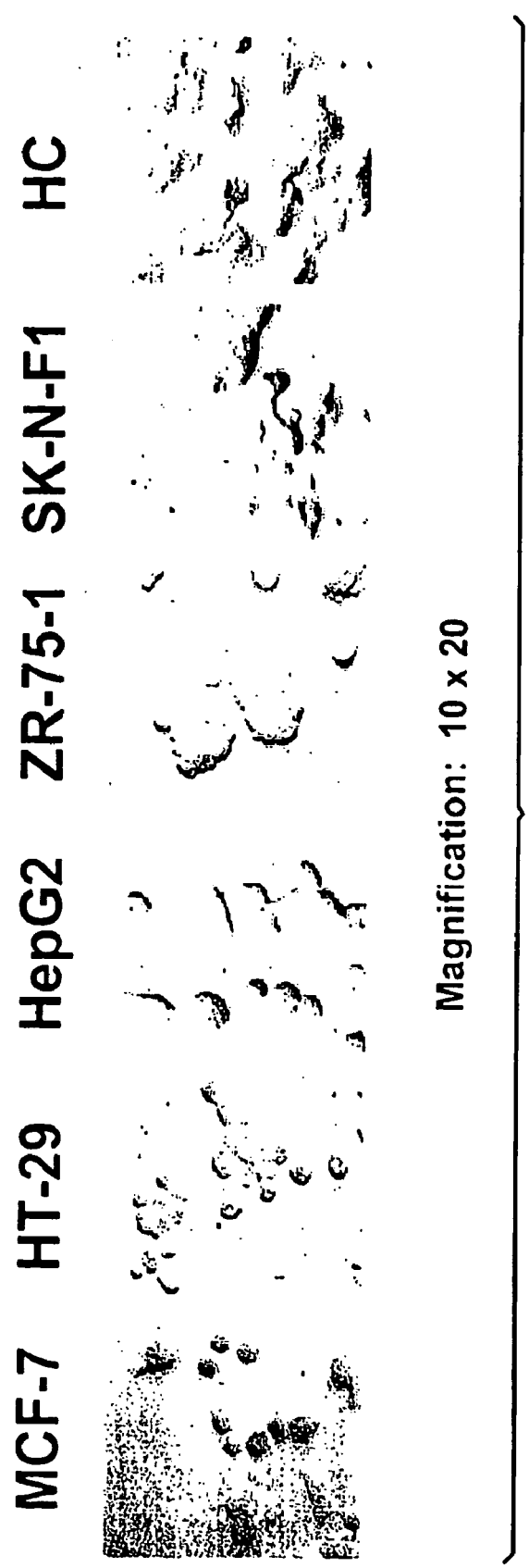
Figure 2C:

Oncogenic transformed or established cancer cells derived from human and fish (MCF-7, HT-29, HepG2, ZR-75-1, SK-N-F1, or HC cells) were plated in their respective serum-free basal medium supplemented with 0.8 $\mu$M of the trout recombinant Ea-4-peptide, with the control protein, or with 2.5 nM of the recombinant hIGF-I and the cultures were examined 24 hours later under an inverted microscope equipped with differential interference phase contrast objectives. While individual cells in the serum-free medium supplemented with control protein, with or without hIGF-I treatment, exhibited rounded morphology and were loosely attached to the culture dish, cells treated with the rtEa-4-peptide were flattened out and attached tightly to the culture dish (FIG. 2). The rtEa-4 peptide treated cells developed several pseudopodia-like structures to establish contact with neighboring cells similar to that seen in untransformed or non-malignant cells.

Because each of these tumor cell lines obtained from ATCC contains a mixed population of tumorous and nontumorous cells, only between 25-40% of the cells from each cell line responded to induction by rtEa-4-peptide. To clarify the question of whether every cell could respond to rtEa-4-peptide, single-cell clones that were shown to be malignant were isolated from the mixed population of ZR75-1 and MDA-MB 231 cell lines and subjected to tests for morphological changes induced by the rtEa-4-peptide. About $1-2 \times 10^5$ cells resuspended in their respective basal medium without FBS were plated in a 6-well culture chamber. Different amounts of trout Ea-4-peptide (0.4 $\mu$M, 0.8 $\mu$M and 1.6 $\mu$M) or control protein (1.6 $\mu$M) were added to the wells, and the cell cultures were incubated at 37.degree. C. under a humidified atmosphere of 5% $CO_2$. Twenty-four hours after initiation of the treatment, cells were observed under an Olympic inverted microscope equipped with phase contrast objective lenses (200.times. magnification).

Figure 3A:
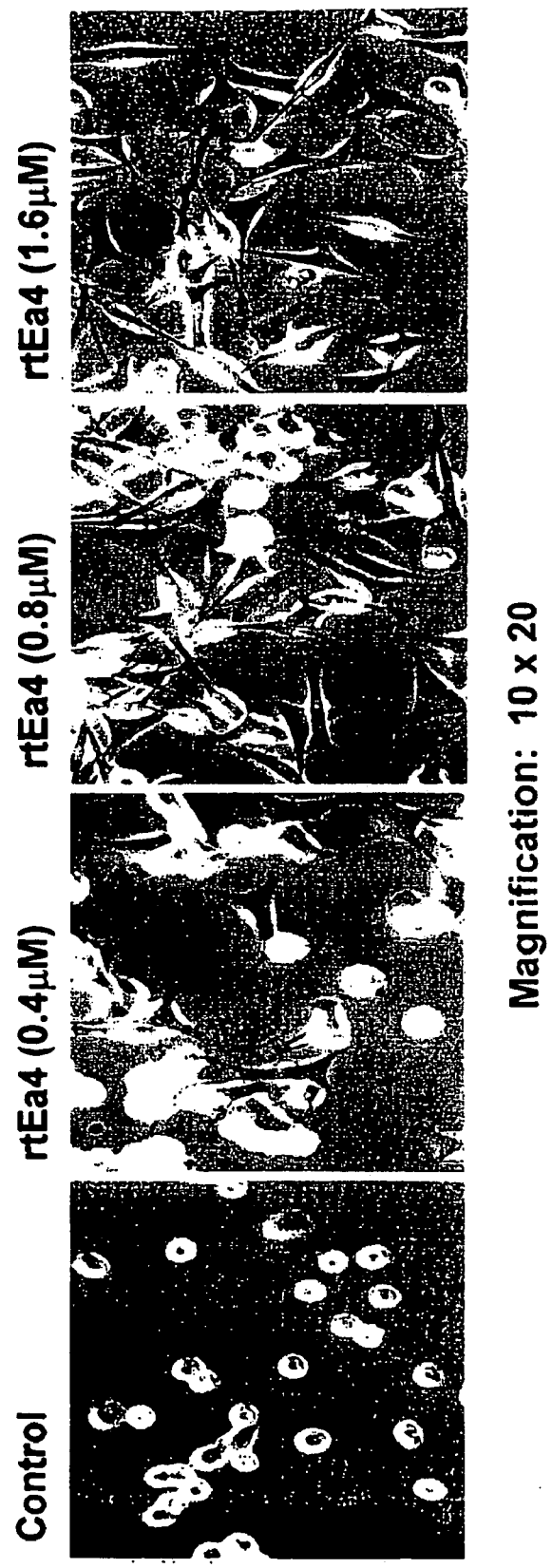
FIG. 3 A-B, depicts morphological changes in the homogenous population of MDA-MB-231 and ZR-75-1 cells induced by exposure to the Ea-4-peptide of trout pro-IGF-I.
Figure 3B:
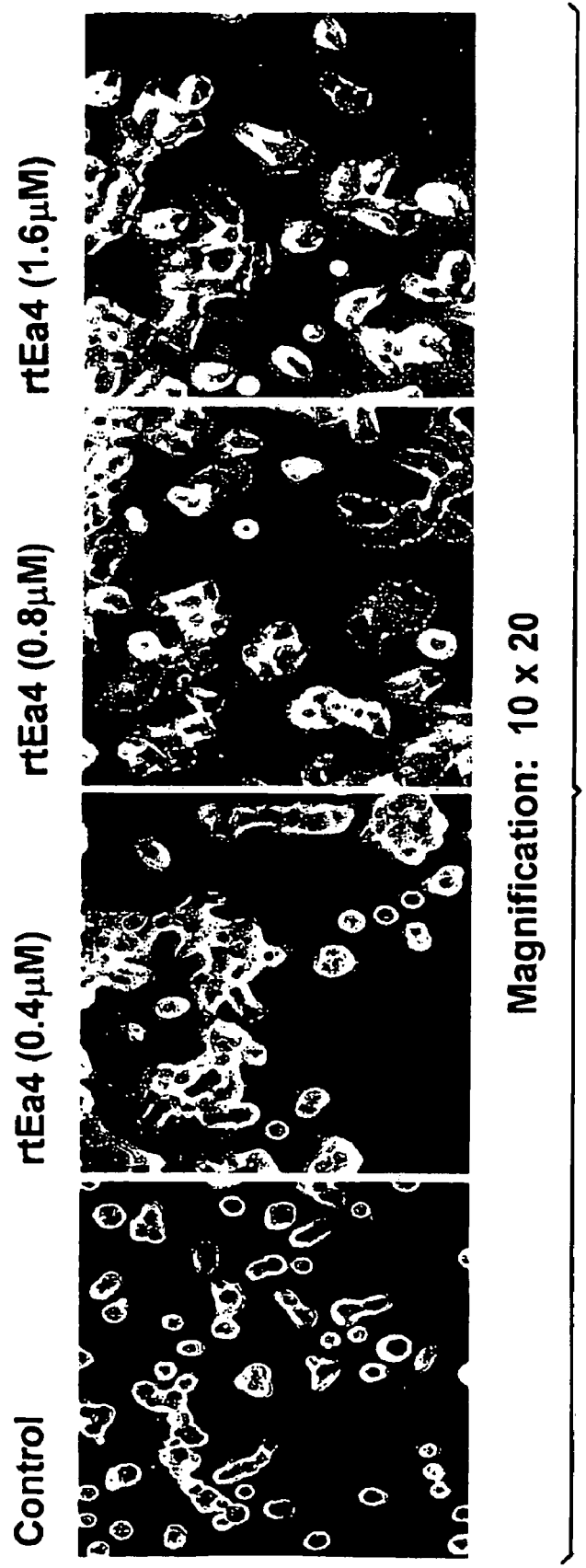

As shown in FIG. 3, almost 95% of the cells from each purified cell line were responsive to treatment with rtEa-4-peptide. The extent of the morphological change was proportional to the amounts (0.4 to 1.6 .mu.M) of rtEa-4-peptide supplemented in the medium (FIG. 3).

Example 5

Effect of Inhibition of mRNA and Protein Synthesis on Morphological Changes

To study the effects of .alpha.-aminitin and cycloheximide, known inhibitors of RNA and protein synthesis, respectively, on morphological changes induced by rtEa-4-peptide, about 1-2.times.10.sup.5 of ZR-75-1 and 293GP cells, re-suspended in their respective basal medium without FBS, were plated in a 6-well culture chamber. Prior to plating the cells, an acid-washed coverslip was placed in each well of the culture chamber. Each culture was treated with recombinant trout Ea-4-peptide at 0.8 .mu.M, and with either .alpha.-aminitin at 10 .mu.g/mL (an RNA synthesis inhibitor) or with cycloheximide at 1.0 .mu.g/mL (a protein synthesis inhibitor). The cell cultures were incubated at 37.degree. C. under a humidified atmosphere of 5% CO.sub.2. Coverslips were removed from the culture chamber 24 hours after initiation of the treatment and observed under an Olympic inverted microscope equipped with differential interference phase contrast objective lenses (final magnification, 200.times.). The viability of the inhibitor-treated cells was further determined by a dye extrusion assay.

Figure 4A:
FIG. 4 A-B, illustrates the effect on induced morphological changes of exposure to RNA- or protein-synthesis inhibitors in cells transformed with nucleic acid encoding trout Ea-4-peptide.
Figure 4B:
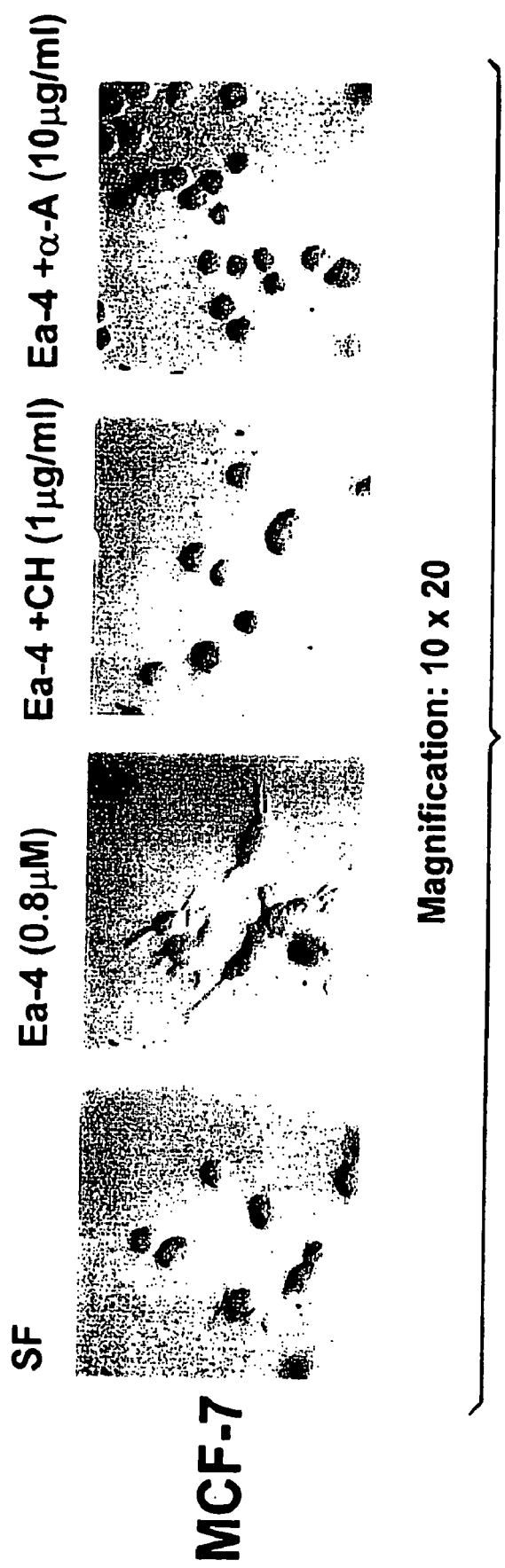

To determine whether the morphological changes induced by the Ea-4 peptides requires synthesis of new proteins or of RNA, 293GP and MCF-7 cells were cultured under the same conditions as described above. Ea-4 peptide-induced morphological changes in 293GP and MCF-7 cells were abolished by treatment with cycloheximide or .alpha.-aminitin (FIG. 4). These results suggest that the morphological change induced by the Ea-4 peptide might result from expression of genes that were activated and/or inactivated during oncogenic transformation or tumor development. This conclusion is further substantiated by results of studies on microarray screening of a collection of human EST's that indicate that the Ea-4 peptide up- and/or down-regulated the expression of a series genes related to cell attachment, proliferation and invasion of MDA-MB-231 cells.

Relative Activity of Trout Ea-2, Ea-3, and Ea-4 Peptides

In examining the biological activity of E-peptides of human pro-IGF-1, the present inventors have determined that hEb peptide (SEQ ID NO:1), like rainbow trout Ea-4 SEQ ID NO:2) peptide, evidences novel and unique activities, apart from the know functions of mature IGF-1. The in vitro effective concentration of synthetic hEb peptide (0.4-3.2 µM) is within a similar range as that of the recombinant rtEa-4 peptide.

Figure 5A:
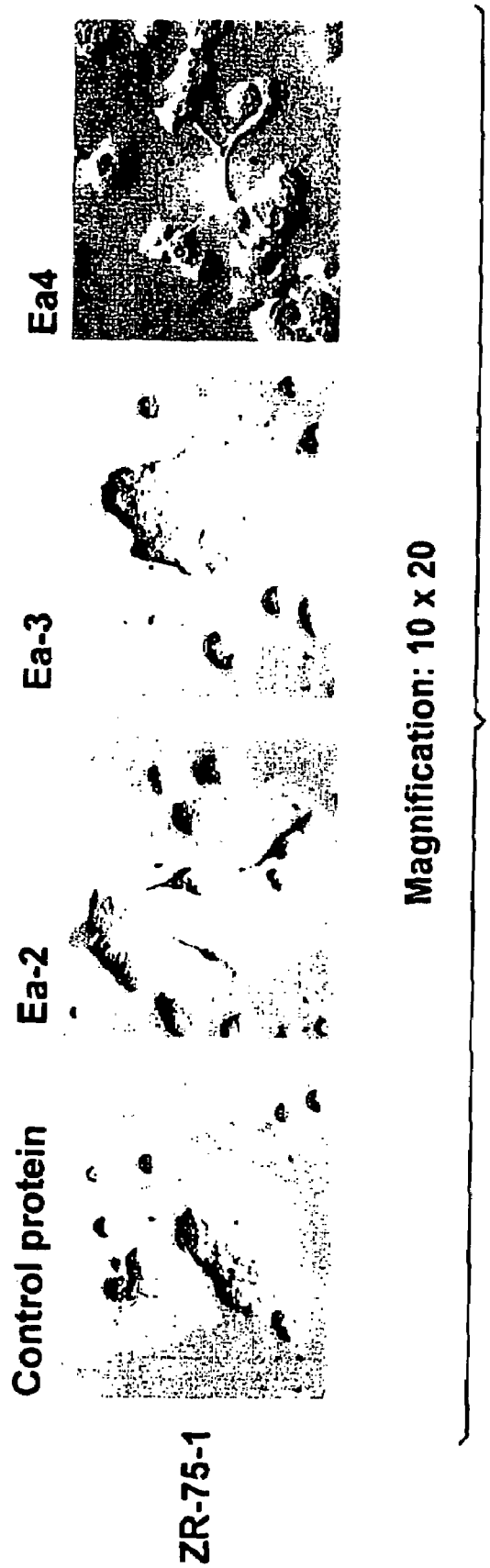
FIG. 5 A-B, demonstrates the effect of exposure to Ea-2, Ea-3, and Ea-4 peptides on the induction of morphological change in ZR-75-1 (A) and 293GP cells (B).
Figure 5B:
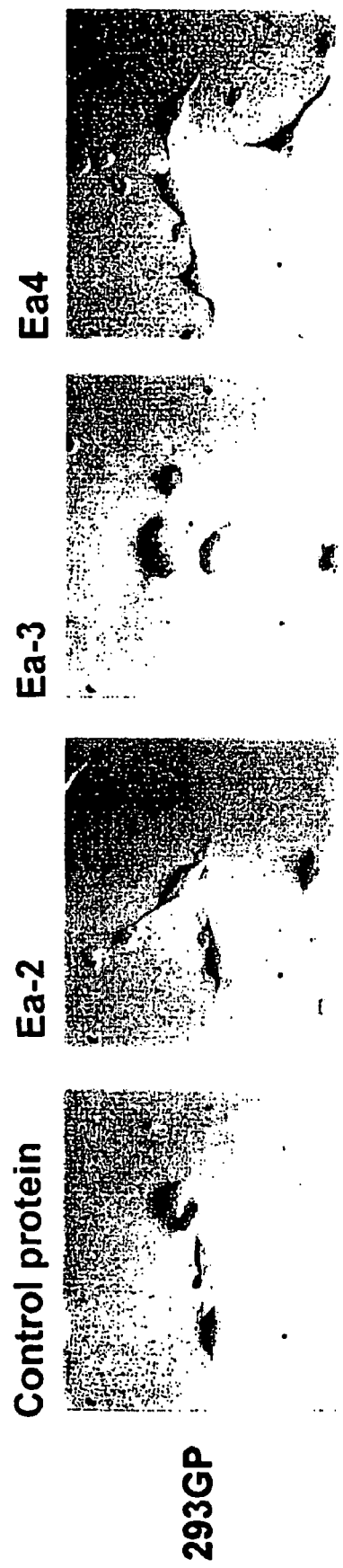

Cells were again cultured as described above. Twenty-four hours after treatment with 0.8 .mu.M of E-peptides or the control protein, the cells were observed under an Olympic inverted microscope equipped with differential interference phase contrast objective lenses (200.times. magnification). Although both Ea-2- and Ea-4-peptides were able to induce morphological change in 293GP or ZR-75-1 cells, the Ea-3 peptide failed to induce any visible morphological change under the identical culture conditions (FIG. 5). This observation indicates that the domain of the E-peptide responsible for the induction of morphological change in the 293GP or ZR-75-1 is not present in the Ea-3-peptide. To confirm this hypothesis, synthetic peptides specific to Ea-1-, Ea-2-, Ea-3- and Ea-4-peptide (Ea-1sp, Ea-2sp, Ea-3sp and Ea-4sp) specific sequence (see FIG. 1) were prepared and tested for their activities to induce morphological change in ZR-75-1 cells.

Figure 6:
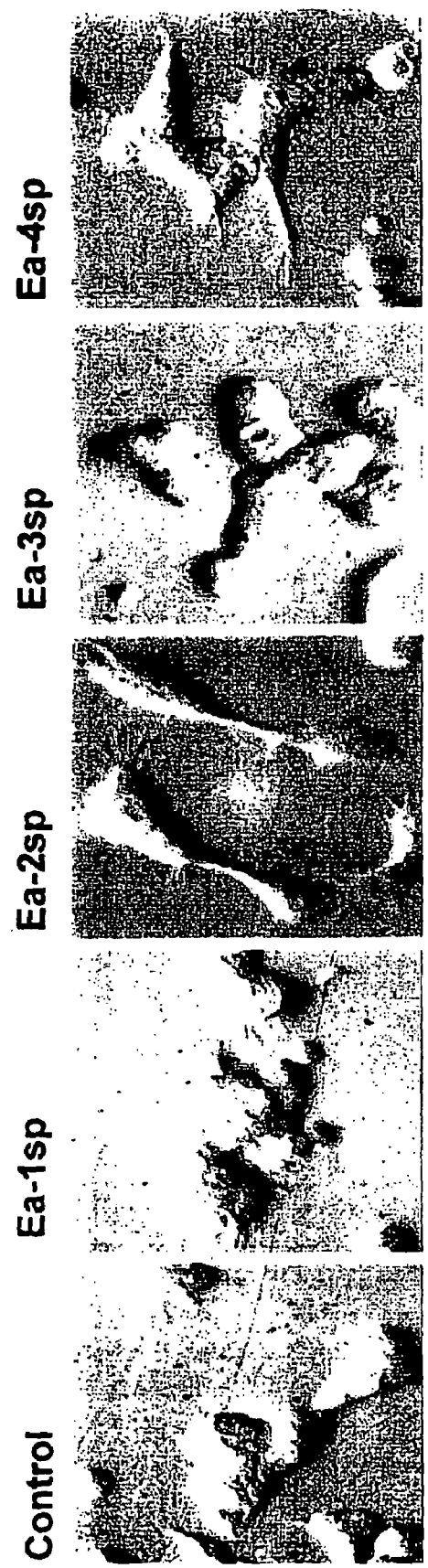
FIG. 6 shows the effect of synthetic peptides containing Ea-1sp, Ea-2sp, Ea-3sp or Ea-4sp specific sequences on induction of morphological change in ZR-75-1 cells.

For FIG. 6, cells were cultured in F12/DME medium without FBS as described above. Twenty-four hours after treatment with 0.8 .mu.M of synthetic peptide containing Ea-1 sp, Ea-2sp, Ea-3sp or Ea-4sp specific sequence or the control protein, the cells were observed under an Olympic inverted microscope equipped with differential interference phase contrast objective lenses (200.times. magnification).

As shown in FIG. 6, Ea-2sp and Ea-4sp, but not Ea-1sp and Ea-3sp at 0.4 .mu.M were able to induce the expected morphological change. These results indicate that the active domain of the Ea-peptide resides within the 12 amino acid residues of Ea-2-peptide.

Example 6

Morphological Changes and Inhibition Assays with Neuroblastoma Cells Using Human Eb Peptide Neuroblastoma SK-N-F1 cells (10.sup.5) were seeded into 12-well culture plates in DMEM/F12 (1:1) supplemented with 0-3.2 .mu.M of synthetic hEb-peptide, or buffer control, and incubated at 37.degree. C. in a 5% CO.sub.2 humidified incubator.

For inhibition studies, cells were pre-incubated with vehicle (0.1% DMSO), or 10-50 mu.M of the MEK inhibitor PD98059 (Promega, Madison, Wis.), or 10 nM-1 .mu.M of the PI-3K inhibitor wortmannin (Sigma), or 10-50 .mu.M of LY294002 (Promega, Madison, Wis.), for one hour prior to the addition of 3.2 .mu.M hEb-peptide.

Cell images were taken by random sampling at various time points using a MicroMAX CCD camera (Princeton Instruments, Bozeman, Mont.). Approximately 1000 cells were analyzed from each treatment, carried out in triplicate. Cells with neurites longer than one cell body diameter (>20 .mu.m for SK-N-F1 cells) were scored as positive neurite-bearing (Fagerstrom, et al., Cell Growth Differ., 7: 775-85, 1996; Morrione, et al., Cancer Res. 60: 2263-72, 2000). The percentage of neurite-bearing cells and the respective length of neurites were measured with reference to a stage micrometer and analyzed using the public domain NIH Image program (developed at the U.S. National Institutes of Health and available on the Internet at http://rsb.info.nih.gov/nih-image).

Morphological Differentiation (Neurite-Like Growth) in Neuroblastoma Cells

SK-N-F1 neuroblastoma cells are characterized as poorly differentiated embryonal cells with an epithelial-like morphology. In examining the biological activities of synthetic hEa and hEb peptides of pro-IGF-I, the present inventors determined that hEb peptides induce morphological changes in SK-N-F1 cells, whereas synthetic hEa-peptide (FIGS. 11A-b), like mature IGF-I (FIGS. 11A-e), lacks this activity. Cells treated with the mature hIGF-I (5 nM) remained rounded and formed aggregated clusters (FIGS. 11A-e), similar to the morphology of the control cells (FIGS. 11A-a), and that of the cells treated with 3.2 .mu.M synthetic hEa-peptide alone (FIGS. 11A-b), or in combination with 5 nM hIGF-I (FIG. 11A-f). In contrast, SK-N-F1 cells treated with synthetic hEb-peptide (1.6 .mu.M or 3.2 .mu.M) differentiated into a neuron-like morphology with one or multiple neurite-like processes and a relatively small cell body (FIGS. 11A-c and 11A-d). The treatment of mature hIGF-I and hEb-peptide combined further enhanced the formation of neurite-like processes (FIGS. 11A-g and 11A-h), and resulted in a 20-30% increase in the percentage of neurite-bearing cells at 1-4 hours after stimulation (quantitative data not shown). The activities of hEb-peptide are identical to those of rainbow trout Ea-4-peptide demonstrated above.

To further characterize the dose-response relationship and time course of hEb peptide in inducing neurite-like process outgrowth, SK-N-F1 neuroblastoma cells were treated with various amounts (0 to 3.2 .mu.M) of hEb peptide over a course of 72 hours. Images of cells were taken by random sampling after 1 h, 6 h, 24 h, 48 h and 72 h of incubation (see FIG. 11B). The average length of neurite-like process outgrowth was measured by random sampling of more than 1000 cells at various time points. The neurite-like processes started to be visible as early as 0.5-1 hour after the addition of hEb peptide. The effect of hEb peptide in inducing neurite-like outgrowth was dose-dependent, as evident from a comparison of cells treated with 0.4 .mu.M hEb peptide with those treated with 0.8-3.2 .mu.M hEb peptide over 24-72 hours. The maximum effect of hEb peptide was observed 48 hours after the addition of 3.2 .mu.M hEb peptide, with an average neurite length of 50 to 60 .mu.m (Table 1, below).

TABLE 1

DOSE RESPONSE AND TIME COURSE STUDIES ON hEb-PEPTIDE INDUCED NEURITE GROWTH

| [hEb-peptide] | Neurite length (μm)‡ | | | | |
|---|---|---|---|---|---|
| (μM) | 2 h | 6 h | 24 h | 48 h | 72 h |
| 0 | 19 ± 0.1 | 21 ± 4.6 | 24 ± 2.2 | 24 ± 0.3 | 24 ± 1.3 |
| 0.4 | 30 ± 1.6 | 31 ± 7.6 | 29 ± 5.2 | 35 ± 0.9 | 32 ± 3.1 |
| 0.8 | 33 ± 2.1 | 36 ± 0.6 | 38 ± 3.9 | 43 ± 1.0 | 41 ± 2.5 |
| 1.6 | 33 ± 3.8 | 38 ± 3.5 | 39 ± 1.8 | 47 ± 3.9 | 48 ± 2.8 |
| 3.2 | 33 ± 2.8 | 39 ± 2.2 | 45 ± 1.7 | 52 ± 3.7 | 48 ± 2.7 |

‡neurite length shown as mean ± standard deviation determined from more than 1000 cells sampled in triplicate at each time point; a dose-response relationship was observed when comparing cells treated with 0.4 μ · M hEb-peptide and those treated with 0.8-3.2 μM hEb-peptide with statistical differences (P ≦ 0.05) from 24-72 hours; the maximum effect of hEb-peptide was obseved at 48 h after initiation of treatment.

In examining the biological activity of E-peptides of human pro-IGF-1, the present inventors have determined that hEb peptide, like rainbow trout Ea-4 peptide, evidences novel and unique activities, apart from the known functions of mature IGF-I. The in vitro effective concentration of synthetic hEb peptide (0.4-3.2 .mu.M) is within a similar range as that of the recombinant rtEa-4-peptide.

Example 7

Effects of Trout Ea-4 Peptide on Colony Formation

An obvious change in the characteristics of normal cells after oncogenic transformation is the loss of contact inhibition and anchorage-dependent cell division behavior (Kosaki et al., 1999). This behavioral change in oncogenic transformed or established cancer cells can be easily demonstrated in vitro by a colony formation assay in a semi-solid medium (Dickson et al., 1986).

Colony formation assays were conducted following the method described by Yang (1975). About 2.times.10.sup.4 of HT-29 (colon cancer cells) or MDA-MB-231 cells (aggressive breast cancer cells) at log phase were plated in their respective basal medium containing 1.25% FBS and 0.5% purified agar (Difco laboratories), and supplemented with various concentrations (0.4 to 1.6 .mu.M) of the recombinant rainbow trout Ea-4 peptide, or the same amount of the control protein, in 6-well culture chambers. After the medium is solidified, each well is overlaid with 1 mL of the basal medium (containing 1.25% FBS) supplemented with same concentration of the trout Ea-4 peptide. The plates were incubated at 37.degree. C. in a humidified incubator with 5% CO.sub.2 and examined daily under an inverted microscope for 2-3 weeks. Colonies were observed under an Olympic inverted microscope equipped with phase contrast objective lenses (final magnification: 40.times.). Colonies with sizes .gtoreq.50 .mu.m were scored. The viability of cells at the conclusion of the experiment was confirmed by dye extrusion assay with tryptan blue. The assay was conducted two times.

Figure 7:
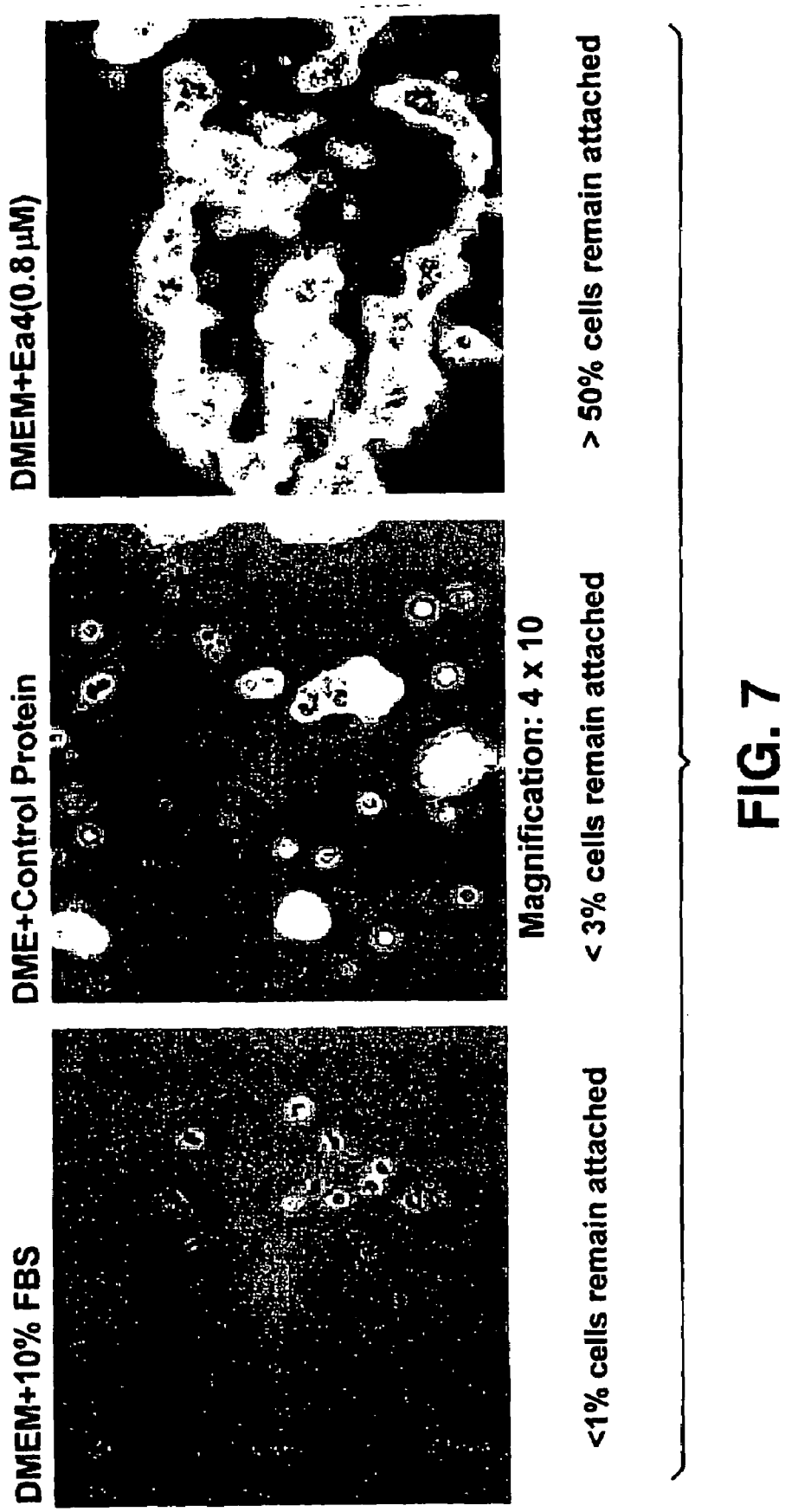
FIG. 7 shows the effect of trout recombinant Ea-4-peptide on attachment of 293GP cells.

To confirm whether treatment of transformed cells with the Ea-4 peptide could result in increased attachment of the cells to the culture dish, 293GP cells were cultured in a serum-free basal medium supplemented with Ea-4-peptide (0.8 .mu.M) or 10% FBS, respectively, in 6-well culture chambers. After four days, the culture medium was removed, and cells were rinsed twice with PBS containing 0.02% EDTA, fresh PBS was added, and the culture plates shaken 20 times manually. At the end of shaking, cells cultured in serum-free medium or medium supplemented with FBS detached completely from the culture chamber, while cells cultured in the serum-free medium supplemented with Ea-4 peptide remained attached to the culture chamber (FIG. 7). These results clearly showed that rtEa-4 peptide enhances the attachment of oncogenic transformed cells to the culture chamber, similar to the behavior exhibited by untransformed (normal) cells.

Figure 8B:
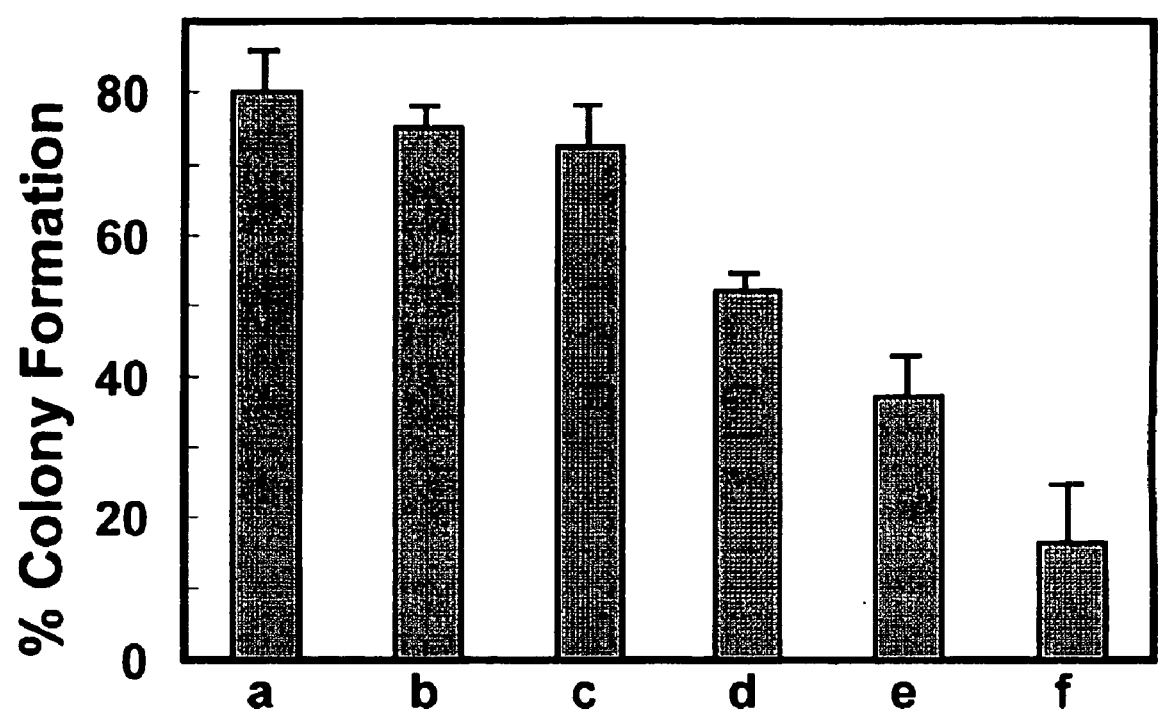
FIG. 8 represents the effect of Ea-4-peptide on colony formation activity of HT-29 and MDA-MB-231 cells in a semi-solid medium. Colonies with sizes >50 .mu.m were scored. A: colony observed in soft agar medium; B: % of colony formation in MDA-MB-231 cells cultured under various medium conditions: a—10% FBS; b—1.25% FBS; c—1.25% FBS and 1.6.mu.M control protein; d–1.25% FBS and 0.4 .mu.M Ea-4-peptide; e–1.25% FBS and 0.8 .mu.M Ea-4-peptide; and f–1.25% FBS and 1.6 .mu.M Ea-4-peptide. Each data point was the average of three samples and the assay was conducted twice.

It has been suggested that the malignant growth property of human neuroblastoma cells can be associated with their differentiation status (Martin, et al., J. Pediatr. Surg. 3: 161-64, 1968). Spontaneous resolution has in fact been observed as a result of neuronal differentiation of neuroblastoma cells in vivo (Pahiman, et al., Eur. J. Cancer., 31A: 453-58, 1995). As shown in FIGS. 8A and 8B, many visible colonies were developed from both cancer cell lines grown in the soft agar medium supplemented with 1.25% FBS and the control protein, but fewer colonies were developed from both cell lines cultured in the same medium supplemented with increasing concentrations of recombinant Ea-4 peptide. These results showed that Ea-4 peptide is able to reduce or abolish the anchorage-independent cell division behavior of tumor cells.

Example 8

Effects of hEb Peptide on Colony Formation

Poor differentiation and anchorage-independent cell growth are among the hallmarks of poor prognosis in neuroblastoma disease. As discussed above, neuroblastoma cells present a unique system in which the relationship between differentiation and tumorigenesis might be successfully dissected. Loss of proper differentiation is a common theme in cellular transformation in many different types of cancer. Thus, inducing cellular differentiation and intervening growth factor signaling have now been discussed as novel alternative approaches to cancer treatment (Garattini and Terao, Curr. Opin. Pharma., 1: 358-63, 2001; Favoni, de Cupis, Pharmcol. Rev., 52: 179-206, 2000). According to the present invention, hEb peptide, like rainbow trout Ea-4 peptide, induces morphological differentiation in neuroblastoma cells.

Figure 12:
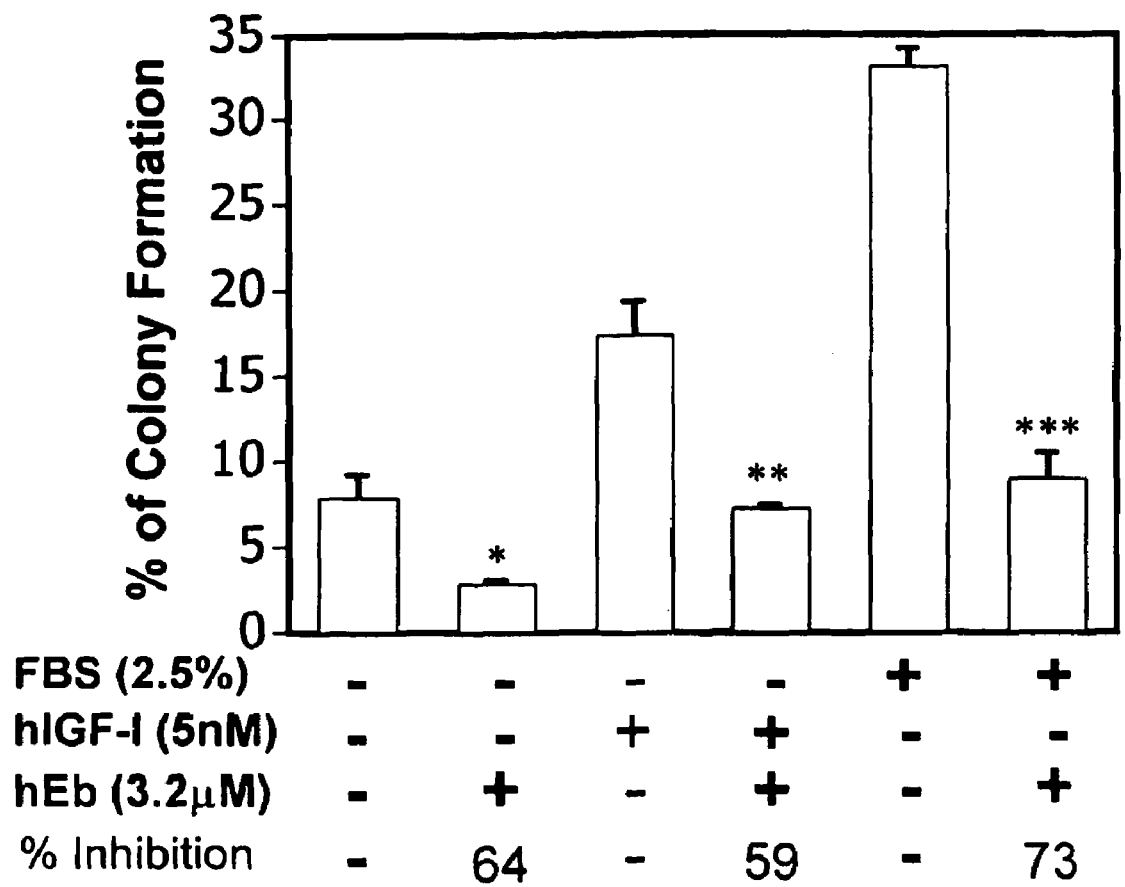
FIG. 12 shows the effects of hEb-peptide on in vitro colony formation in neuroblastoma SK-N-F1 cells.

The effect of hEb-peptide on in vitro colony formation was tested in the presence or absence of either the mature hIGF-I or fetal bovine serum (FIG. 12). Human neuroblastoma SK-N-F1 cells (10.sup.4) were mixed with 0.4% soft agar supplemented with or without hEb peptide (3.2 .mu.M), IGF-I (5 nM) and/or fetal bovine serum (2.5%), as indicated. The cell mixtures were seeded on top of a solidified basal medium DMEM/F12 (1:1) containing 0.5% agar. Medium supplemented with various peptides or serum were overlaid on top of the solidified cell layer followed by a two-week period incubation at 37.degree. C. in a 5% CO.sub.2 humidified incubator. The percentage of cells formed into colonies with a diameter greater than 100 .mu.m Macpherson, Tissue culture methods and applications, pp 276-80: N.Y. Academic Press, 1973) were scored in triplicate and subjected to Student t-test analysis. At least three independent assays under each treatment conditions were carried out.

As expected, mature hIGF-I (5 nM), like fetal bovine serum (FBS, 2.5%) strongly stimulated colony formation in neuroblastoma cells (SK-N-F1) (FIG. 12). On the other hand, hEb-peptide (3.2 .mu.M) significantly reduced the percentage of cells grown into colonies with a diameter greater than 100 .mu.m. In the absence of serum and growth factors, inhibition of colony formation by hEb peptide was 64%, similar to that in the presence of hIGF-I (5 nM) (59% inhibition). Colony formation in the presence of FBS (2.5%) was inhibited by 73%. According to the present invention, in a manner similar to that demonstrated for rtEa-4 peptide, the hEb peptide of human pro-IGF-I exhibits an inhibitory effect on anchorage-independent growth by 59-73%. This activity is in sharp contrast to the stimulatory effect of mature IGF-I.

Figure 13:
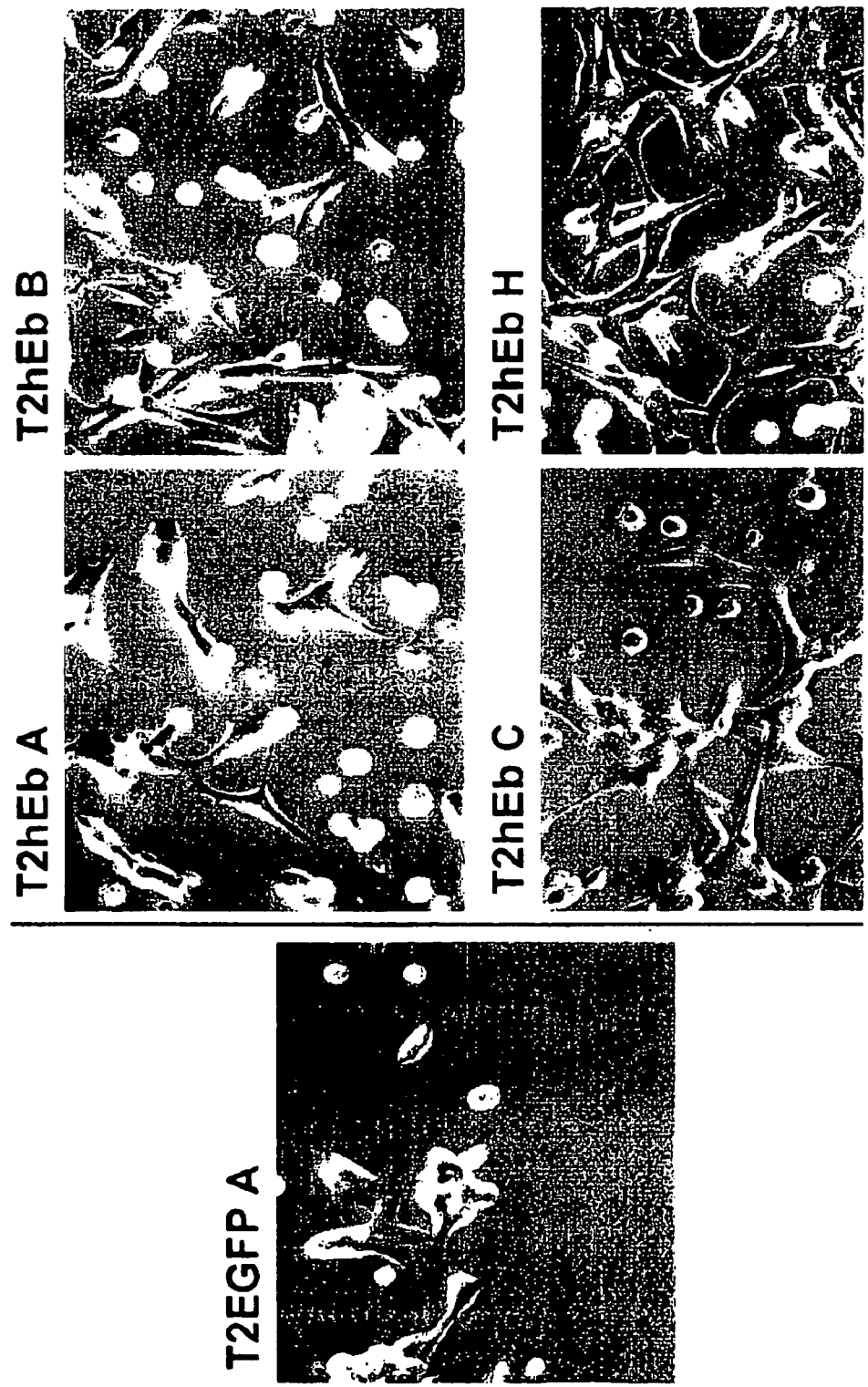
FIG. 13 shows the morphological change of MDA-MB-231 cells transfected with hEb cDNA.
Figure 14:
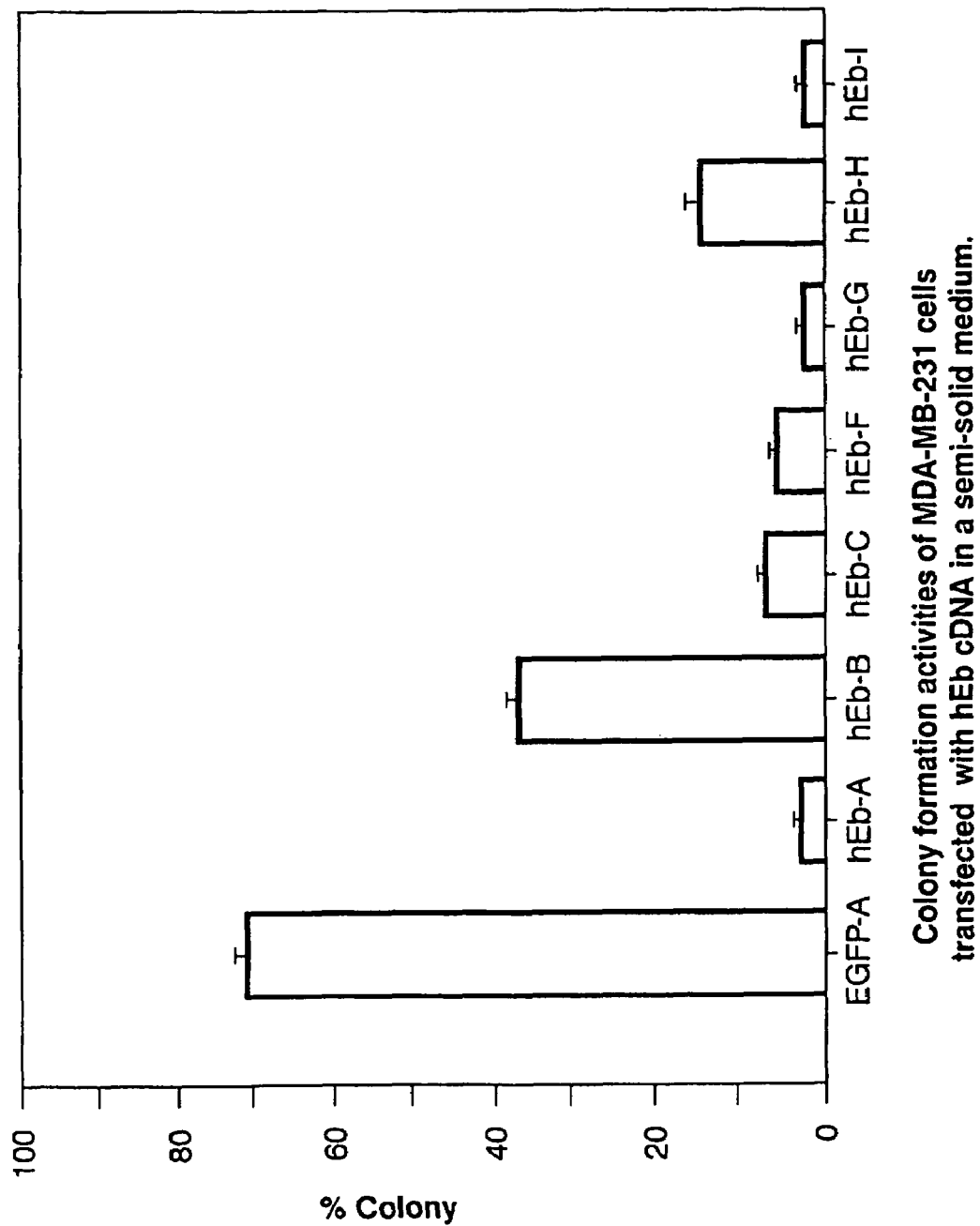
FIG. 14 shows the colony formation activities of MDA-MB-231 cells transfected with hEb cDNA in a semi-solid medium.
Figure 15B:
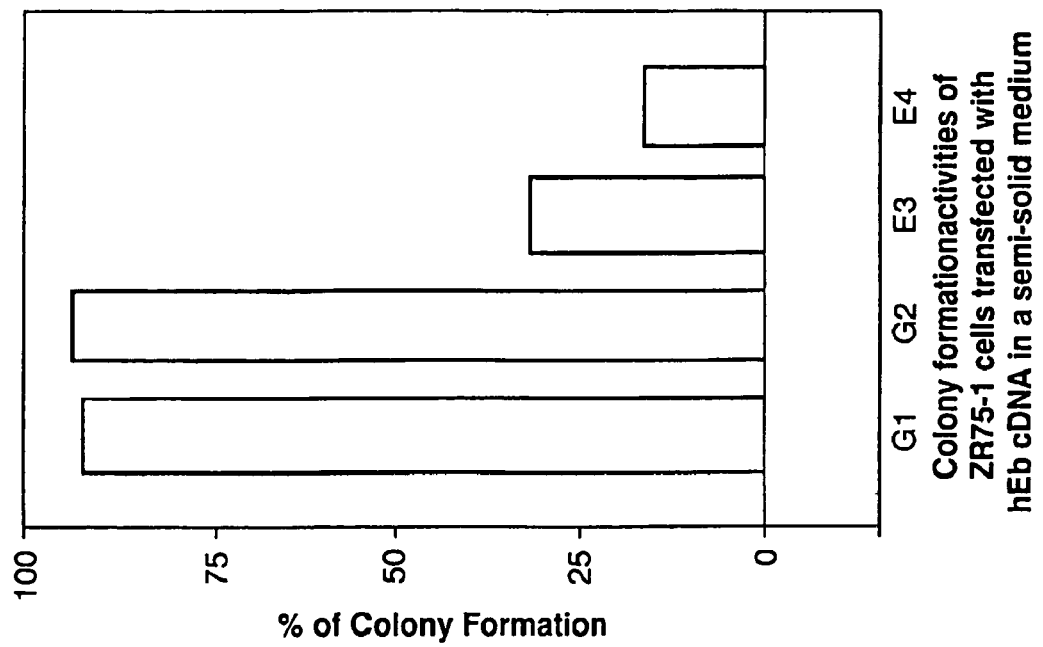
FIG. 15 depicts colony formation activities of ZR-75-1 cells transfected with hEb cDNA in a semi-solid medium. A: GFP activities in different transfectants; B: colony formation activities of different transfectants. G1 and G2, EGFP control transfectants; E3 and E4, hEb/EGFP transfectants.
Figure 15A:
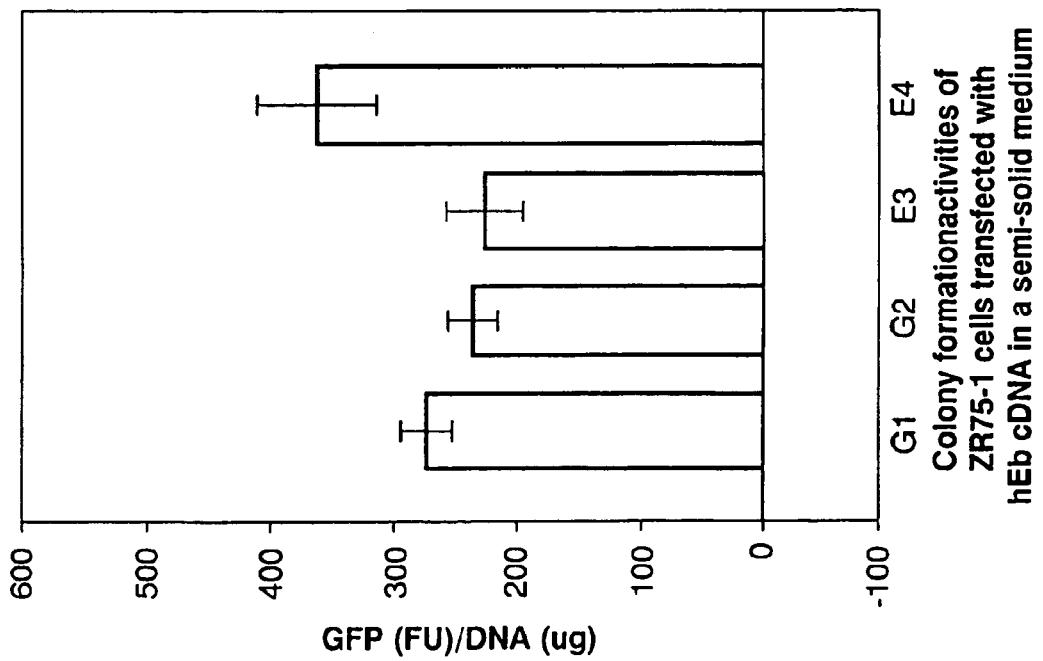

To further confirm the effect of hEb-peptide on reduction or elimination of malignant growth of cancer cells, aggressive breast cancer cells, MDA-MB-231 and ZR-75-1 cells, were transfected with a hEb-peptide gene construct. As shown in (FIG. 13), the morphology of hEb gene transfected cells, namely hEb A, hEb B, hEb C and hEb H, exhibited a morphology similar to that of untransfected MDA-MB-231 treated with synthetic hEb-peptide. Furthermore, results of the colony formation assay showed that, like treatment of cancer cells with synthetic hEb-peptide, the colony formation activities of hEb gene transfected cells were greatly reduced or diminished completely (FIGS. 14 and 15).

Normally, adherent cells require anchorage to extracellular matrix (ECM) to survive and proliferate. This anchorage dependency is primarily mediated by integrins that are responsible for engaging cell-ECM interaction and thus activating the growth- and survival-promoting signals. Tumor cells, including neuroblastoma cells, are generally resistant to apoptosis induced by loss of attachment to ECM and cannot only survive but grow independently of anchorage. According to the present invention, the hEb peptide of human pro-IGF-I restores the anchorage dependency for cell survival and cell division in neuroblastoma cells. These results suggest, without limiting the present invention, that hEb-peptide induced signaling may act collaboratively and converge with extracellular adhesion signaling pathways in regulating cell survival and division. The results provided herein also indicate that the hEb peptide, but not the hEa peptide of human pro-IGF-I induces morphological differentiation and inhibits anchorage-independent growth in human neuroblastoma cells. A similar nature and range of biological activities have been shown with Ea-4 peptide of rainbow trout pro-IGF-I. Thus, E-peptides of pro-IGF-I are not only biologically active but are functionally conserved in fish and humans. Furthermore, the data disclosed herein also indicate, without limiting the scope of the present invention, that these conserved E-peptide activities might be mediated by conserved signal transduction mechanisms.

Example 9

Invasion Assays

An obvious characteristic of cancer cells is their ability to invade normal tissues (metastasis) by migrating to other locations and subsequent colonization. The molecular events of metastasis have become clearer in recent years. These events involve the secretion of metalloproteases by tumor cells, digestion of basement membrane (invasion), and migration and colonization of cancer cells in new locations (Clezardin 1998). The invasive behavior can be demonstrated by an in vitro invasion assay where the migration of cancer cells across a semi-solid Matrigel (proteins isolated from basement membranes) is measured. To investigate whether the Ea-4-peptide of trout pro-IGF-1 can retard the invasive activity of cancer cells, an in vitro invasion assay was conducted in HT1080 cells, a known invasive cancer cell line, in the presence of Ea-4-peptide.

Invasion assays were conducted in BIOCOAT MATRIGEL invasion chambers following the procedure provided by Becton Dickinson Labware (Bedford, Mass.; 40480 and 40481 guidelines). According to these procedures, 1.times.10.sup.6 of HT1080 cells in DMEM supplemented with 1.25% FBS, with Ea-4 peptide (0.17 .mu.M and 0.34 .mu.M), or the same amount of the control protein, were plated in each insert of the Matrigel or control invasion chambers. The inserts were placed in the respective chambers containing DMEM medium supplemented with 10% FBS, and the chambers were incubated at 37.degree. C. under a humidified atmosphere of 5% CO.sub.2 for 24 hours. After removal of the non-invaded cells with cotton swabs, the invaded cells on the other side of the membranes were stained with the Diff-Quick T stain (Becton Dickinson Labware, Bedford, Mass.) and observed under an Olympic inverted microscope (magnification, 200.times.). Control proteins were prepared from *E. coli* cells carrying the expression plasmid without the Ea-4-peptide gene by the same purification method (Tian et al., 1999). The assay was repeated three times.

As shown in Table 2, below, treatment of HT-1080 cells with trout Ea-4-peptide results in a dose-dependent reduction of the invasive activity of HT 1080 cells.

TABLE 2

EFFECT OF Ea4-PEPTIDE ON THE INVASION ACTIVITY OF HT-1080 CELLS[1]

| Treatment | # invaded cells/view (MIC)[2] | # invaded cells/view (CIC)[3] | % Invasion[4] | % Reduction of invasion |
|---|---|---|---|---|
| NoEa-4 | 63 ± 13 | 157 ± 6 | 40 | 0 |
| Control | 62 ± 5 | 157 ± 6 | 39 | 2 |
| Ea-4(0.17 μM) | 30 ± 5 | 157 ± 6 | 19 | 52 |
| Ea-4(0.34 μM) | 24 ± 1 | 157 ± 6 | 15 | 62 |

[1]Assay conducted in BIOCOAT MATRIGEL invasion chambers following procedure provided by Becton Dickson Labware (Bedford, MA, guidelines #40480 and #40481).
[2]MIC: mean number of invaded cells per view invaded throughMatrigel insert membrane; each cell number determined as average of three independent counting; reported ± standard deviation of the mean.
[3]CIC: mean number of cells pre view migrated through control insert membrane; each cell number determined as average of three independent counting; reported ± standard deviation of the mean.
[4]% invasion = mean # cells invading through Matrigel insert membrane / mean · cells invading through insert membrane.

Example 10

Anti-Angiogenesis Activity of the Trout Ea-4 Peptide

The term, angiogenesis, as used herein, refers to the generation of new blood vessels in a tissue or an organ. Under normal physiological conditions, angiogenesis is invoked under controlled, specific situations. In disease states, however, the control is altered and pathological damage can occur. It is known that the growth and spread of solid tumors, such as breast cancer, depends on angiogenesis. In view of the role of angiogenesis in cancer and other diseases, it is desirable to have a means of reducing or inhibiting the process. It is hoped that anti-angiogenetic agents will stop the growth of cancer cells by blocking the blood supply and thus preventing the formation of new vessels that feed the cancerous cells. The activity of the peptides on angiogenesis were compared to a known anti-angiogenetic agent, endostatin. Endostatin, a proteolytic cleavage product of type XVIII collagen, is a potent angiogenesis inhibitor. The protein is a specific inhibitor of endothelial proliferation and angiogenesis, as described in U.S. Pat. No. 5,854,205, hereby incorporated by reference.

Figure 16A:
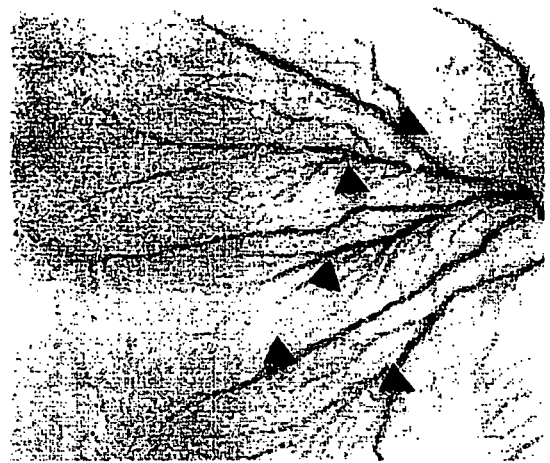
FIG. 16A. shows the CAM membrane and its branch points as indicated by arrows.
Figure 16B:
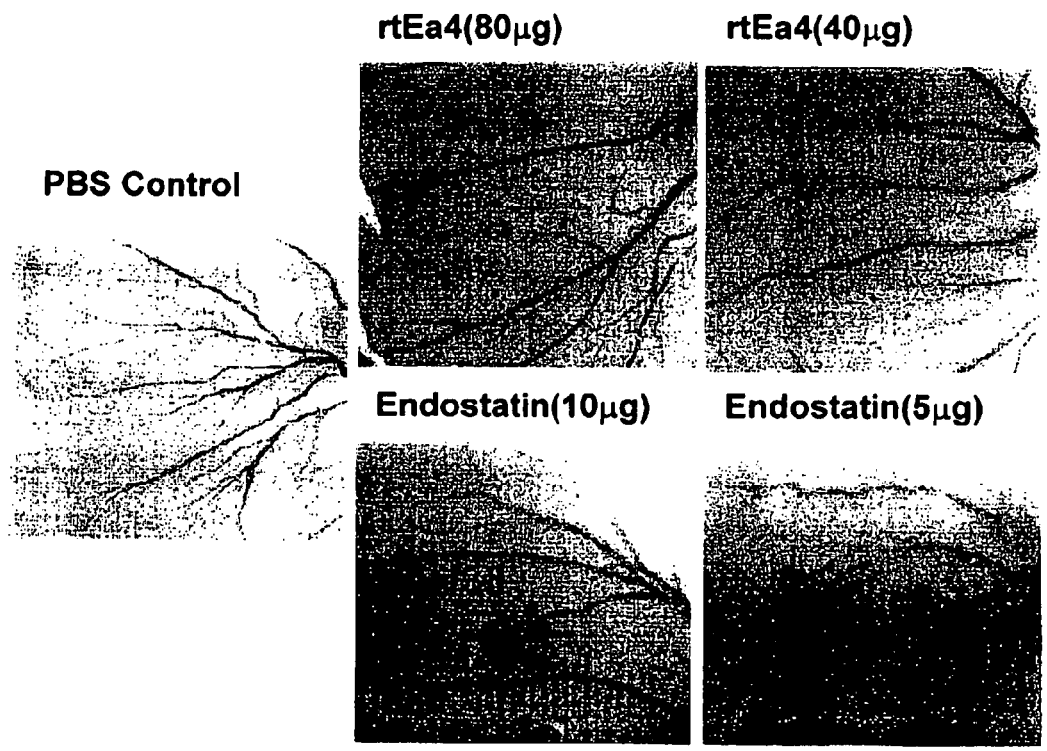
FIG. 16B shows the comparative effects of Ea-4 and endostatin on blood vessel development.
Figure 17:
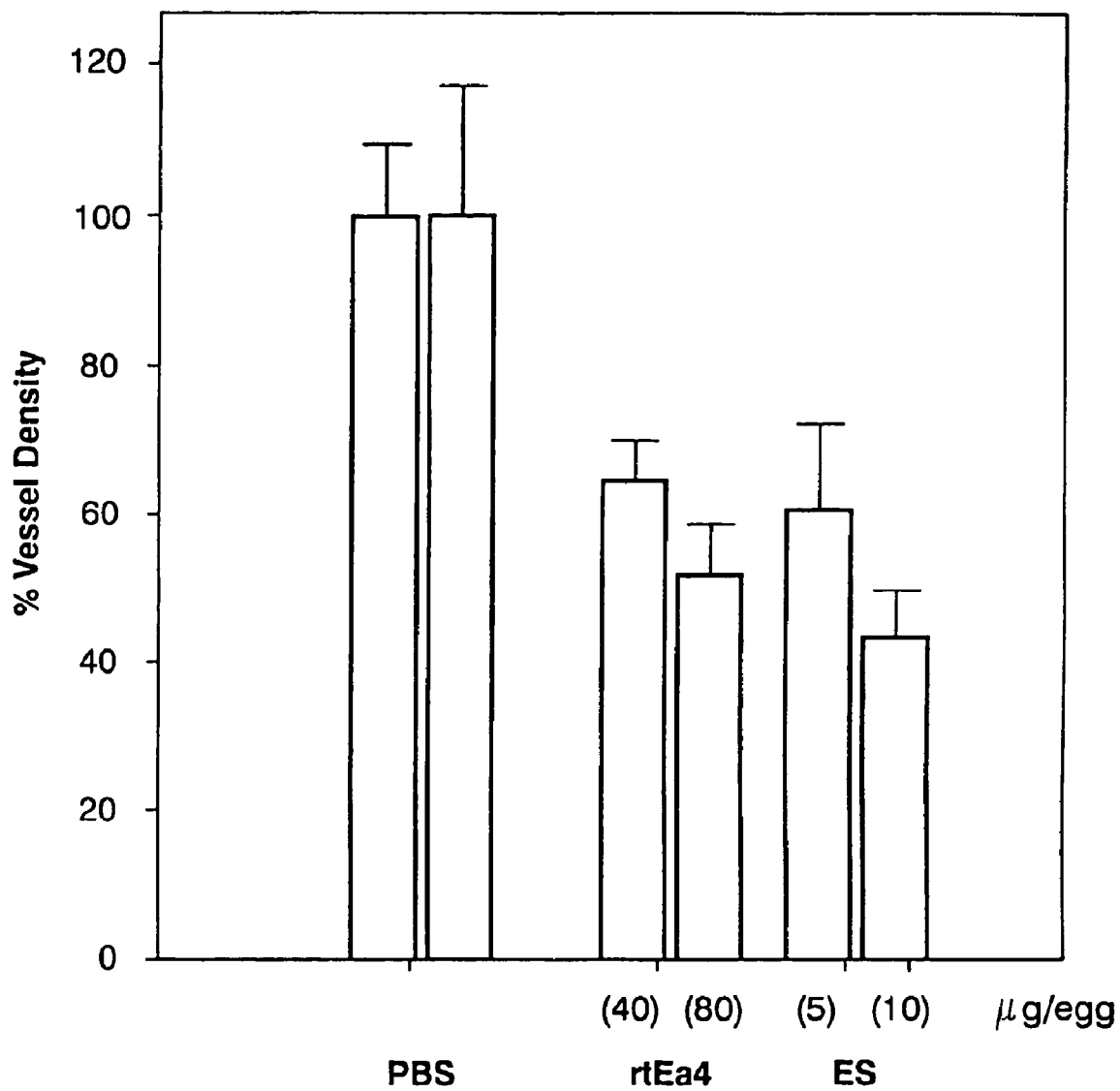
FIG. 17 is a histogram illustrating the quantitative effect of exposure to Ea-4 peptide and to endostatin on vessel density.

A suitable assay is the chick embryo chorioallantoic membrane (CAM) assay described by Crum et al. Science 230: 1375 (1985). See also, U.S. Pat. No. 5,001,116, hereby incorporated by reference, which describes the CAM assay. Briefly, the Ea-4 peptide (40 .mu.g and 80 .mu.g), endostatin (5 .mu.g and 10 .mu.g) and a PBS control buffer were delivered onto the chorioallantoic membrane (CAM) of three-day old chick embryos. The CAMs were photographed in ovo with a digital camera on day 7. The angiogenic response was assessed by counting the number of intersect points of the blood vessels spread out in a defined field (vessel density). FIGS. 16A-B shows the inhibitory effect of the Ea-4 peptide on blood vessel branching. The effect is quantified in the histogram in FIG. 17.

Example 11

Anti-Angiogenesis Activity of the hEb Peptide

Each were dissolved in PBS, and various and known amounts of hEb-peptide (250 .mu.g, 500 .mu.g and 1000 .mu.g respectively) and human endostatin (10 .mu.g and 20 .mu.g respectively) were applied to the CAM. Pictures were taken on day 7 for vessel density determination. FIG. 18 shows the percent vessel density as a measure of peptide. The extent of inhibition of angiogenesis on CAM was scored from the defined area of CAM shown in FIG. 19.

The anti-angiogenic effect of hEb-peptide was measured on chorioallantoic membranes of chick embryos. As shown in FIGS. 18 and 19, hEb-peptide exerts a dose-dependent reduction of vessel density in the chorioallantoic membrane of chicken embryos.

Example 12

Using the widely accepted chicken cancer model, we recently discovered the seeding of aggressive human breast cancer cells, for example MDA-MB-231, on the chorioallantoic membrane (CAM) of five day old chicken embryos resulted in rapid growth and invasion of the cells and induction of blood vessel formation around the MDA-MB-231 cell mass in the chicken embryos. The invasion of MDA-MB-231 cells in the chicken embryos was further confirmed by immunocytochemistry. The rapid growth and invasion of MDA-MB-231 cells and the induction of blood vessel formation by MDA-MB-231 cells on chicken CAM are inhibited by treatment with a single or multiple doses of rtEa4- or hEb-peptide was also demonstrated by the chicken CAM assay. Further analysis revealed the surprising and unexpected result that E-domain peptides possess activity to kill cancer cells by inducing apoptosis. The activity in the widely accepted chicken model, provides ample support for the belief that the methods of the invention can be used to treat cancer in animals as well as humans.

Figure 20:
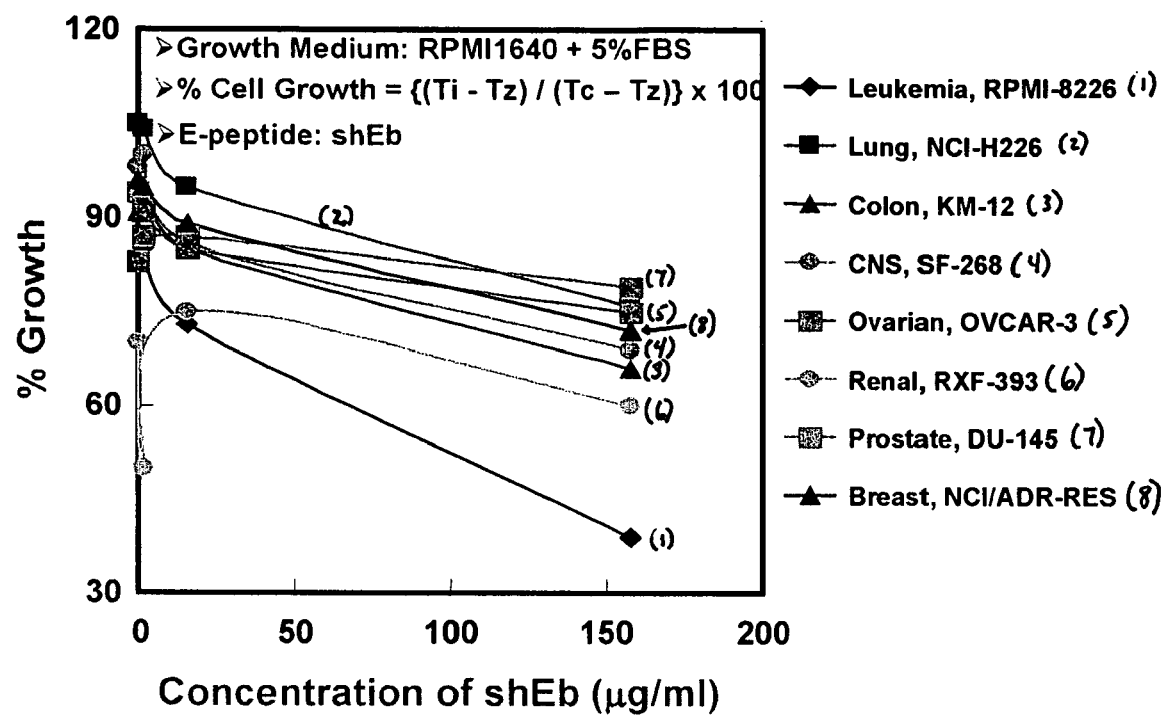
FIG. 20 depicts the effects of synthetic hEB-peptide on killing of various human cancer cells. About $1 \times 10^6$ cells of cancer cells were seeded in each well of a 96-well plate and various amounts of synthetic hEb-peptide were added as indicated. The cells were cultured for about 48 hours and the % of cell growth was determined.

Killing of Cancer Cells by E-Domain Peptides, In Vitro:

About $1 \times 10^6$ cells of various human cancer cell lines were seeded in each well of a 96-well culture plate with various amounts of synthetic human Eb-peptide (shEb-peptide). It is specifically contemplated by the inventors that in any of the examples of the preferred embodiments described herein, synthetic or recombinant E domain peptides can be used. After incubation for about 48 hours, the growth of cells in each well was determined and compared to non-hEb-peptide controls. As shown in FIG. 20, different degrees of killing of cancer cells by shEb-peptide were observed.

Example 13

Induction of Apoptosis by E Domain Peptides

Figure 21:
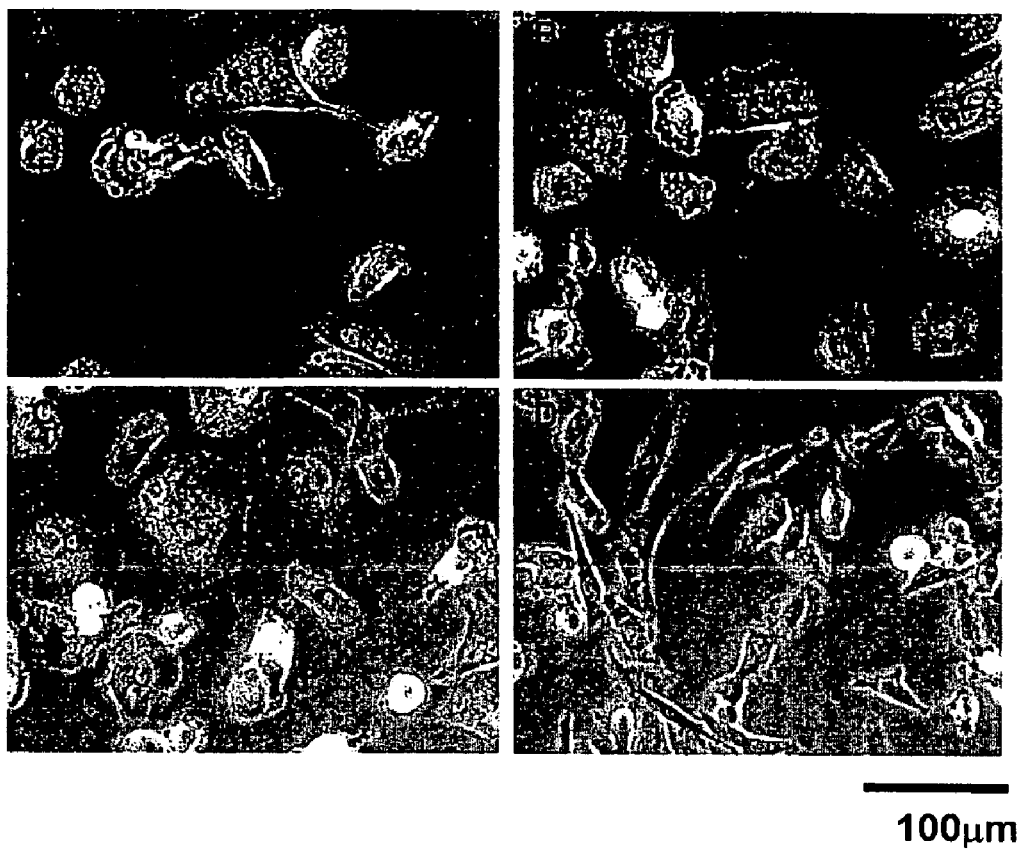
FIG. 21 depicts apoptosis in MDA-MB-231 cells induced by rtEa4-peptide. MDA-MB-231 cells treated with about 1.5 µM of rtEa4-peptide (A, B, and C) or control peptide (D) for about two hours and observed under a microscope. Arrows indicate apoptotic cells.
Figure 22:
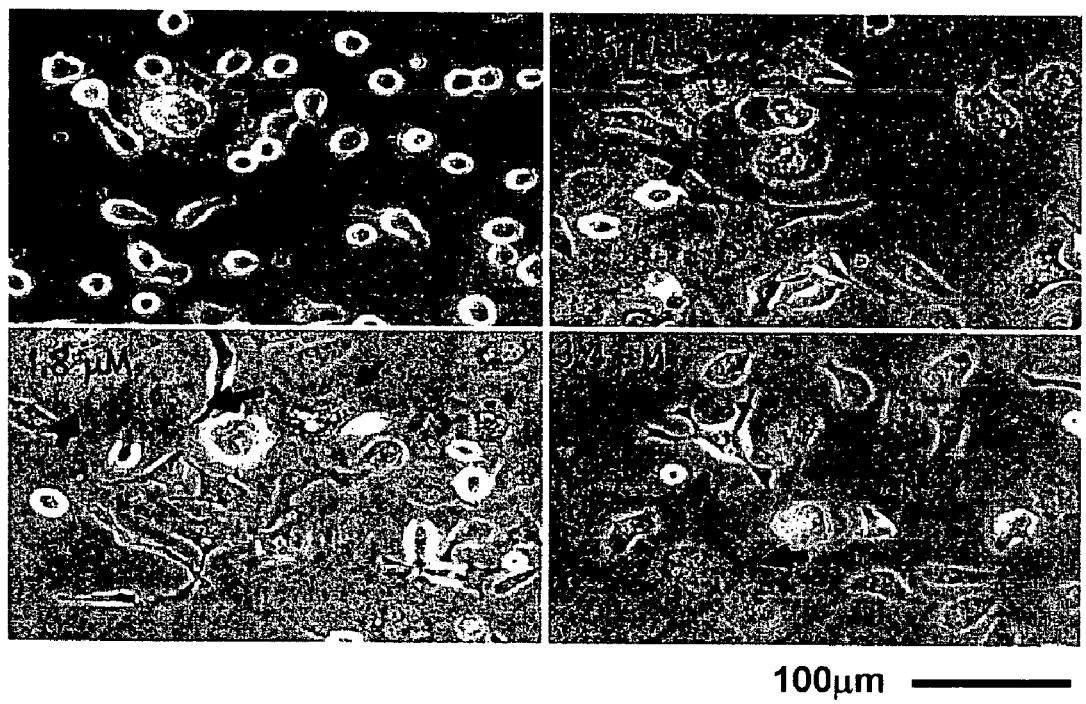
FIG. 22 depicts apoptosis in ovarian cancer cells (SKOV) induced by various amounts of rtEa4-peptide. SKOV cells were treated with various amounts (0.1-3.4 µM) for 4 hours and observed under a microscope. Arrows indicate apoptotic cells.

Killing of cancer cells by E-peptide could be the consequence of apoptosis or necrosis. To differentiate these two possibilities, MDA-MB-231 (C) cells were grown in culture in the presence of about 1.5 µM of trout Ea4-peptide. After about two hours of incubation the cells were observed under a microscope. As shown in FIG. 21, some of the cells (FIG. 21A-C) are going through apoptosis when compared to the control (FIG. 21D). FIG. 22 presents the results of the effect of trout Ea4-peptide on induction of apoptosis in ovarian cancer cells (SKOV-3). A clear dose-dependent induction of apoptosis was observed.

Figure 23:
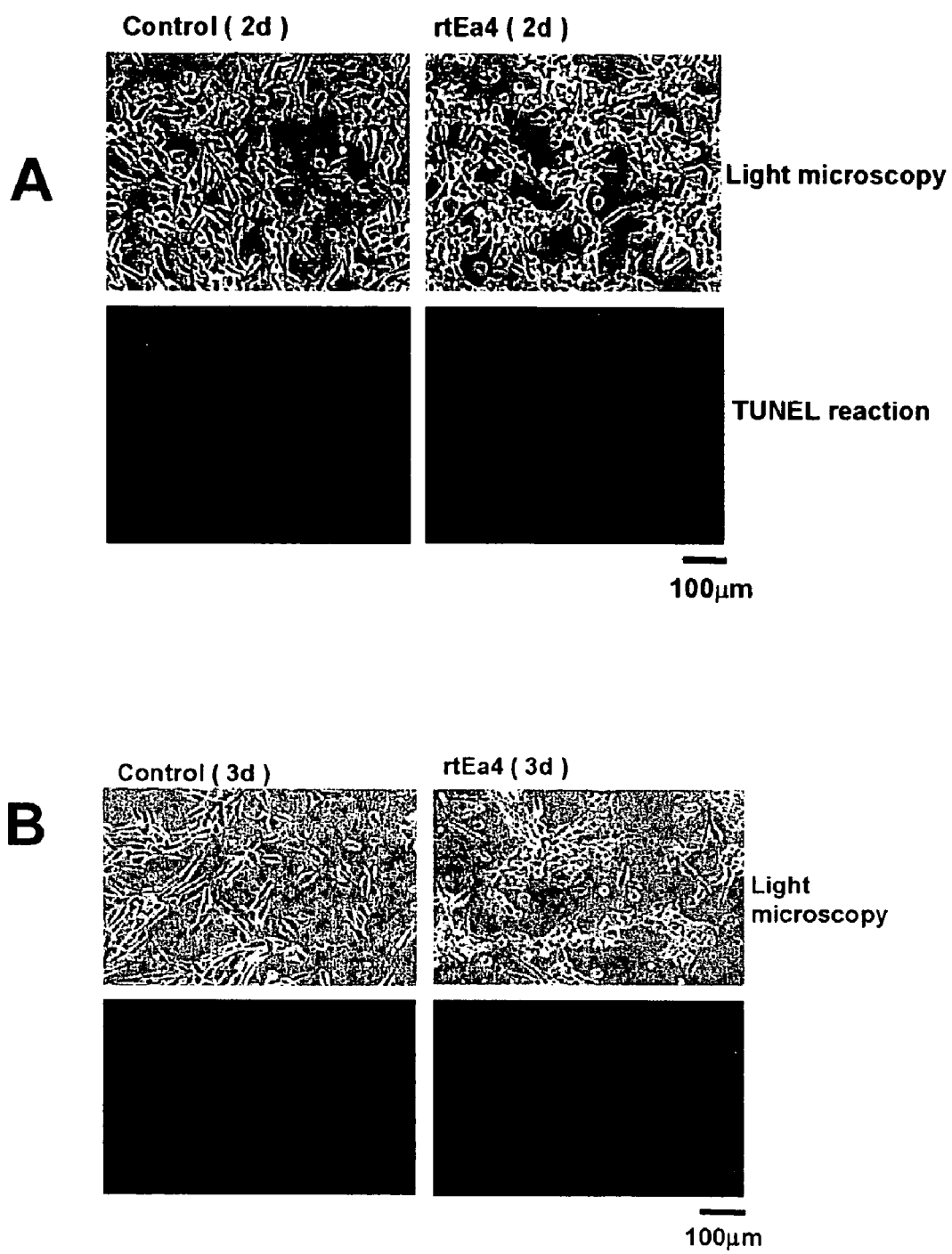
FIG. 23 depicts induction of apoptosis in MDA-MB-231 cells by rtEA4-peptide. MDA-MB-231 cells were treated wit control protein or rtEa4-peptide (about 1.5 µM) for two days, and three days, and were then subjected to TUNEL assay. (A) Treatment with rtEa4-peptide for two days; (B) Treatment with rtEa-4-peptide for three days.

Apoptosis of cells can also be detected by terminal deoxynucleotidyl transferase mediated dUTP nick end labeling (TUNEL) assay. FIGS. 23 and 24A present the results of TUNEL assay on MDA-MB-231(C) cells following treatment with trout Ea4-peptide. TUNEL staining positive cells are observed in MDA-MB-231(C) cells treated with trout Ea4-peptide. The same results were observed in cancer cells such as ovarian cancer cells (OVCAR-3 AND SKOV-3) and small lung cancer cells (NCI-H526 cells) (Table 3). It is interesting to note that E-peptide does not induce apoptosis in non-cancerous cells such as the primary baby foreskin cells (CCD-1112SK) (Table 4).

TABLE 3

EFFECT OF rtEa4-PEPTIDE ON INDUCTION OF CASPASE-3 mRNA.

| rtEa4 (µM) | Caspase-3 mRNA (# molecules / µg total RNA) | | |
| --- | --- | --- | --- |
| | MDA-MB-231 | OVCAR-3(B) | SKOV-3(A) |
| 0 | $1.8 \times 10^5 \pm 3.6 \times 10^4$ | $9.9 \times 10^5 \pm 1.4 \times 10^4$ | $2.4 \times 10^5 \pm 5.8 \times 10^4$ |
| 0.04 | $3.9 \times 10^5 \pm 3.8 \times 10^4$ | $7.8 \times 10^5 \pm 7.9 \times 10^4$ | $3.0 \times 10^5 \pm 3.8 \times 10^4$ |
| 0.20 | $3.4 \times 10^5 \pm 3.1 \times 10^4$ | $9.9 \times 10^5 \pm 2.0 \times 10^4$ | $2.5 \times 10^5 \pm 2.1 \times 10^4$ |
| 1.00 | $4.6 \times 10^5 \pm 9.5 \times 10^4$ | $1.9 \times 10^5 \pm 3.4 \times 10^4$ | $3.7 \times 10^5 \pm 7.1 \times 10^4$ |
| 5.00 | $5.8 \times 10^5 \pm 1.3 \times 10^4$ | $1.0 \times 10^5 \pm 1.4 \times 10^4$ | $2.2 \times 10^5 \pm 2.2 \times 10^4$ |

TABLE 4

EFFECT OF rtEa4- OR hEb-PEPTIDE ON INDUCTION OF APOPTOSIS IN HUMAN CANCER CELLS

| Cancer Cell Lines | Apoptosis |
| --- | --- |
| MDA-MB-231(C) | + |
| SKOV-3(A) | + |
| OVCAR-3(B) | + |
| NCI-H526(F) | + |
| CCD-1112SK[1] | − |

[1]CCD-1112: primary cell line developed from human baby foreskin.

Example 14

Figure 24:
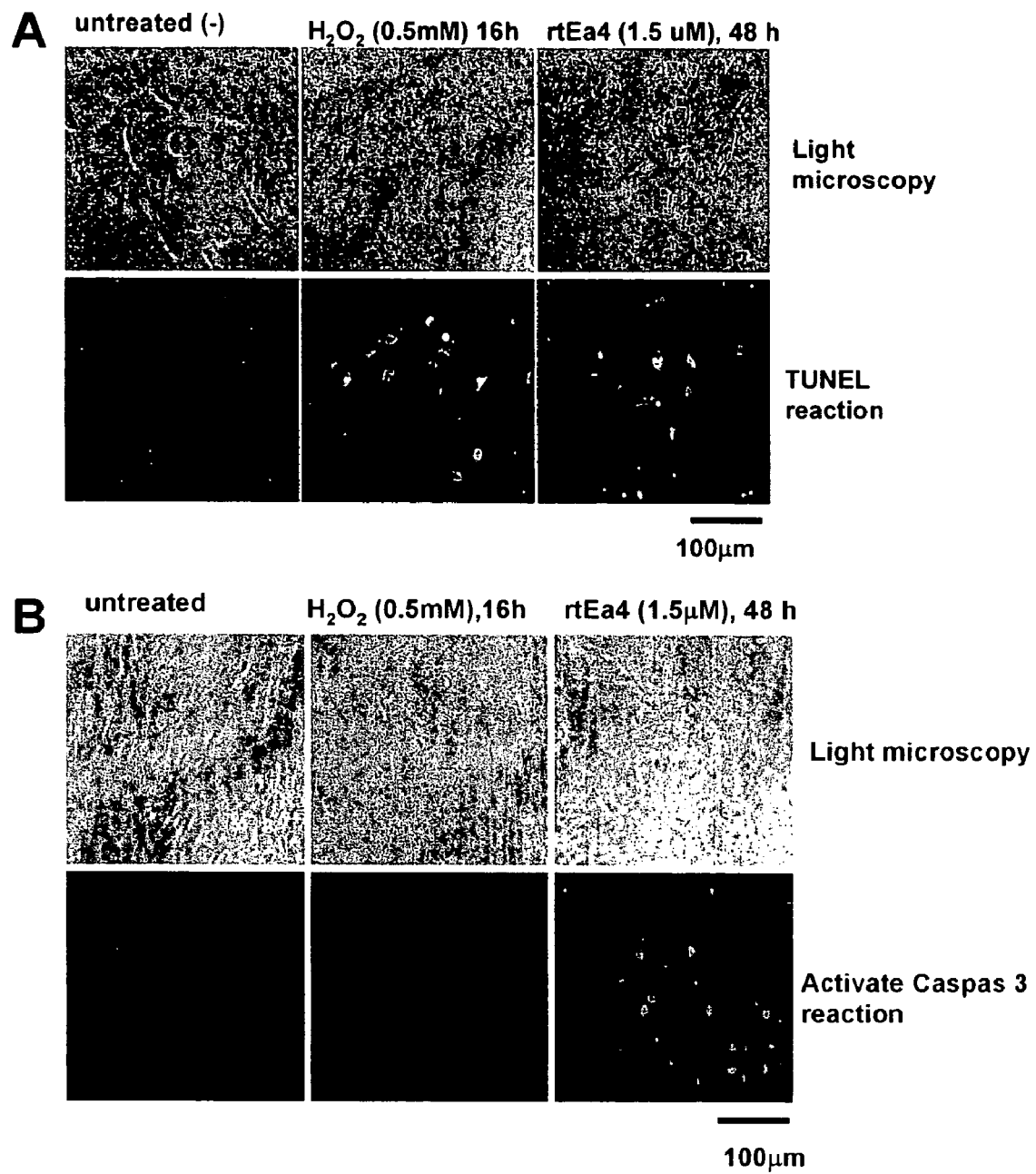
FIG. 24 depicts the effect of rtEa4-peptide on induction of apoptosis in MDA-MB-231 cells treated with rtEa4-peptide. (A) Detection of apoptosis by TUNEL assay; (B) Detection of apoptosis y detecting the induction of the activated caspase-3 activity. MDA-MB-231 cells were treated with about 1.5 µM of rtEa4-peptide for about 48 hours, fixed and subjected to TUNEL assay or stained with anti-human activated caspase-3 serum conjugated with rhodamine. Hydrogen peroxide ($H_2O_2$), 0.5 mM, was used to induce apoptosis as a positive control.

Induction of Caspase-3 mRNA and Levels of Activated Caspase-3 Activity in Cancer Cells by E-Domain Peptide Induction of caspase-3 has been widely used as an indicator of cells undergoing apoptosis. As shown in Table 3, the mRNA levels of caspase-3 in breast cancer cells (MDA-MB-231(C)), and ovarian cancer cells (OVCAR-3 and SKOV-3) are induced by trout Ea4-peptide. Furthermore, the level of activated caspase-3 activity in breast cancer cells (MDA-MB-231(C)) was also induced by trout Ea4-peptide (FIG. 24).

While this invention has been particularly shown and described with references to exemplary and preferred embodiments thereof, it will be understood by those skilled in the art that various changes in form and details may be made therein without departing from the scope of the present invention encompassed by the appended claims.

The invention claimed is:

1. A method for inducing apoptosis in a cancer cell comprising, administering to one or more cancer cells vitro, an effective amount of a composition comprising a peptide selected from the group consisting of an IGF-1 Ea4-domain peptide having the amino acid sequence of SEQ ID NO:2; an IGF-1 hEb domain peptide having the amino acid sequence of SEQ ID NO:1; and a combination thereof, wherein the composition induces cancer cell apoptosis.

2. The method of claim 1, wherein the composition comprises one or more pharmaceutically acceptable adjuvants.

3. The method of claim 1, wherein the composition further comprises an antiangiogenic agent.

4. The method of claim 1, wherein the peptide comprises the IGF-1 Ea-4 domain peptide having the amino acid sequence of SEQ ID NO:2.

5. The method of claim 1, wherein the peptide comprises the IGF-1 hEb domain peptide having the amino acid sequence of SEQ ID NO:1.

6. The method of claim 1, wherein the peptide comprises the IGF-1 Ea-4 domain peptide having the amino acid sequence of SEQ ID NO:2, and IGF-1 hEb domain peptide having the amino acid sequence of SEQ ID NO: 1.

7. The method of claim 1, wherein the peptide is fusion protein.

8. The method of claim 1, wherein the cancer cell is selected from the group consisting of a breast cancer cell, colon cancer cell, neuroblastoma cell, kidney cancer cell, ovarian cancer cell, prostate cancer cell, and combinations thereof.

9. A method for inducing apoptosis in a cancer cell, consisting of administering to one or more cancer cells vitro, an effective amount of an insulin-like growth factor (IGF-1) E-domain peptide having the amino acid sequence of SEQ ID NO:2.

* * * * *